US008912511B2

(12) United States Patent
Schoenborn

(10) Patent No.: US 8,912,511 B2
(45) Date of Patent: Dec. 16, 2014

(54) DEVICE AND METHOD FOR MULTI-PHOTON FLUORESCENCE MICROSCOPY FOR OBTAINING INFORMATION FROM BIOLOGICAL TISSUE

(75) Inventor: Karl-Heinz Guenter Schoenborn, Berlin (DE)

(73) Assignee: W.O.M. World of Medicine AG, Berlin (DE)

(*) Notice: Subject to any disclaimer, the term of this patent is extended or adjusted under 35 U.S.C. 154(b) by 135 days.

(21) Appl. No.: 13/377,395

(22) PCT Filed: Jun. 17, 2010

(86) PCT No.: PCT/EP2010/058576
§ 371 (c)(1),
(2), (4) Date: Dec. 9, 2011

(87) PCT Pub. No.: WO2010/146134
PCT Pub. Date: Dec. 23, 2010

(65) Prior Publication Data
US 2012/0080616 A1    Apr. 5, 2012

(30) Foreign Application Priority Data

Jun. 17, 2009 (DE) .......... 10 2009 029 831

(51) Int. Cl.
F21V 9/16      (2006.01)
G02B 21/00     (2006.01)
A61B 5/00      (2006.01)
G01N 21/64     (2006.01)

(52) U.S. Cl.
CPC ........ G02B 21/0028 (2013.01); G02B 21/0076 (2013.01); A61B 5/0068 (2013.01); A61B 2562/0242 (2013.01); G02B 21/0036 (2013.01); A61B 5/0075 (2013.01); A61B 5/0071 (2013.01); A61B 5/445 (2013.01); A61B 5/0062 (2013.01); A61B 5/443 (2013.01); G01N 21/6458 (2013.01); A61B 5/0059 (2013.01)
USPC ..................................... 250/459.1

(58) Field of Classification Search
CPC ............. A61B 2562/0242; A61B 5/0059; A61B 5/0062; A61B 5/0068; A61B 5/0071; A61B 5/0075; A61B 5/443; A61B 5/445; G01N 21/6458; G02B 21/0028; G02B 21/0036; G02B 21/0076
USPC ........................................ 250/459.1
See application file for complete search history.

(56) References Cited

U.S. PATENT DOCUMENTS 5,034,613 A    7/1991    Denk et al.
5,459,325 A    10/1995   Hueton et al.
(Continued)

FOREIGN PATENT DOCUMENTS

DE    19801139 A1    7/1999
DE    10065146 A1    7/2002
(Continued)

OTHER PUBLICATIONS

EP Office Action dated May 16, 2013 as received in Application No. 10 734 059.8.
(Continued)

Primary Examiner — David Porta
Assistant Examiner — Taeho Jo
(74) Attorney, Agent, or Firm — Maschoff Brennan

(57) ABSTRACT

A device for multi-photon fluorescence microscopy for obtaining information from biological tissue is provided. The device comprising a laser unit for generating an excitation radiation, an optical unit which is formed to focus the excitation radiation for generating an optical signal at different locations in or on an object to be examined, and a detector module for detecting the optical signal from the region of the object. The optical unit for generating the optical signal at different locations in or on the object is movable in at least one direction relative to the object.

14 Claims, 12 Drawing Sheets

(56) References Cited

U.S. PATENT DOCUMENTS

| | | | |
|---|---|---|---|
| 5,780,857 A * | 7/1998 | Harju et al. | 250/458.1 |
| 5,801,881 A * | 9/1998 | Lanni et al. | 359/386 |
| 6,088,097 A | 7/2000 | Uhl | |
| 6,249,630 B1 | 6/2001 | Stock et al. | |
| 6,537,829 B1 * | 3/2003 | Zarling et al. | 436/514 |
| 6,750,457 B2 * | 6/2004 | Heffelfinger et al. | 250/458.1 |
| 6,863,406 B2 * | 3/2005 | Grier et al. | 359/614 |
| 7,079,262 B2 * | 7/2006 | Jones et al. | 356/630 |
| 7,095,556 B2 * | 8/2006 | Iketaki et al. | 359/385 |
| 7,433,119 B2 | 10/2008 | Gugel | |
| 7,496,399 B2 | 2/2009 | Maschke | |
| 7,679,741 B2 | 3/2010 | Dyba et al. | |
| 7,863,585 B2 | 1/2011 | Hell et al. | |
| 8,217,992 B2 * | 7/2012 | Bewersdorf et al. | 348/47 |
| 8,300,669 B2 * | 10/2012 | Dantus et al. | 372/25 |
| 2001/0045523 A1 * | 11/2001 | Baer | 250/459.1 |
| 2003/0161038 A1 * | 8/2003 | Tobben et al. | 359/386 |
| 2006/0011861 A1 * | 1/2006 | Wolleschensky et al. | 250/459.1 |
| 2006/0012785 A1 | 1/2006 | Funk et al. | |
| 2006/0012871 A1 * | 1/2006 | Funk et al. | 359/385 |
| 2006/0058682 A1 * | 3/2006 | Miller et al. | 600/476 |
| 2006/0228725 A1 | 10/2006 | Salafsky | |
| 2007/0159690 A1 * | 7/2007 | Ulrich et al. | 359/385 |
| 2007/0229801 A1 * | 10/2007 | Tearney et al. | 356/73 |
| 2007/0290145 A1 | 12/2007 | Viellerobe et al. | |
| 2008/0081950 A1 | 4/2008 | Koenig et al. | |
| 2008/0205833 A1 | 8/2008 | Fu et al. | |
| 2008/0258077 A1 * | 10/2008 | Baer | 250/458.1 |
| 2009/0046298 A1 * | 2/2009 | Betzig | 356/521 |
| 2009/0067458 A1 | 3/2009 | Ji et al. | |
| 2009/0156429 A1 | 6/2009 | Scott et al. | |
| 2009/0218513 A1 * | 9/2009 | Bec et al. | 250/458.1 |
| 2009/0218516 A1 * | 9/2009 | Gryczynski et al. | 250/459.1 |
| 2009/0290150 A1 | 11/2009 | Takimoto et al. | |
| 2009/0316141 A1 * | 12/2009 | Feldkhun | 356/217 |
| 2010/0102249 A1 * | 4/2010 | Akselrod et al. | 250/459.1 |
| 2011/0057119 A1 * | 3/2011 | Connally | 250/459.1 |
| 2011/0092380 A1 | 4/2011 | Stahler et al. | |

FOREIGN PATENT DOCUMENTS

| | | |
|---|---|---|
| DE | 10347712 A1 | 5/2005 |
| DE | 10252005 B4 | 6/2005 |
| DE | 102004002918 A1 | 8/2005 |
| DE | 102004034977 A1 | 2/2006 |
| DE | 102006009831 A1 | 9/2007 |
| DE | 102006056596 A1 | 6/2008 |
| DE | 102006062089 A1 | 7/2008 |
| DE | 102007039111 A1 | 2/2009 |
| EP | 0807814 A1 | 11/1997 |
| EP | 1929939 A2 | 6/2008 |
| WO | 0160237 A2 | 8/2001 |
| WO | 2007054495 A1 | 5/2007 |

OTHER PUBLICATIONS

Zipfel, et al., "Nonlinear Magic: Multiphoton Microscopy in the Biosciences", Nature Biotechnology, Nov. 2003, vol. 21, No. 11, pp. 1369-1377.

Konig, et al., "High-Resolution Multiphoton Tomography of Human Skin with Subcellular Spatial Resolution and Picosecond Time Resolution", Journal of Biomedical Optics, Jul. 2003, vol. 8, No. 3, pp. 432-439.

Denk, et al., "Two-Photon Laser Scanning Fluorescence Microscopy", Science, vol. 248, No. 6, Apr. 1990, pp. 43-46.

Levene, et al., "In Vivo Multiphoton Microscopy of Deep Brain Tissue", vol. 91, Apr. 2004, pp. 1908-1912.

* cited by examiner

DEVICE AND METHOD FOR MULTI-PHOTON FLUORESCENCE MICROSCOPY FOR OBTAINING INFORMATION FROM BIOLOGICAL TISSUE

CROSS-REFERENCE TO A RELATED APPLICATION

This application is a National Phase Patent Application of International Patent Application Number PCT/EP2010/058576, filed on Jun. 17, 2010, which claims priority of German Patent Application Number 10 2009 029 831.2, filed on Jun. 17, 2009.

BACKGROUND

This invention relates to a device for multi-photon fluorescence microscopy for obtaining information from biological tissue and to a method for multi-photon fluorescence microscopy.

Such device includes a laser unit for generating an excitation radiation, an optical unit which is formed to shape the excitation radiation for generating an optical signal and focus the same at different locations in or on an object to be examined, a detector module for detecting the optical signal from the region of the object, and a signal processing and control module for the signal-technological and algorithmic processing of said optical signal for converting the same into a diagnostically evaluable image signal and for controlling the entire system.

In multi-photon fluorescence microscopy (short: multi-photon microscopy) so-called multi-photon microscopes are used, which are special optical microscopes from the group including laser scanning microscopes. High-resolution microscopic images are generated by utilizing the so-called multi-photon fluorescence (mostly two-photon fluorescence) or the generation of higher harmonics, for example frequency doubling or tripling and as a result the generation of the second or third harmonic (SHG: second harmonic generation; THG: third harmonic generation) of the incident excitation light.

In multi-photon microscopy, a strong focused excitation radiation, mostly generated by a laser, is used to generate non-linear optical effects in a tissue to be examined, which effects are based on the interaction of a plurality of photons (light particles) arriving in a molecule at the same time. The strength of the generated signal does not increase linearly with the number of photons incident per unit time, but with the square (in the case of two-photon effects) or the third power (in the case of three-photon effects). With respect to the entry of the excitation radiation into the tissue, the operation of a multi-photon microscope is similar to that of a confocal laser scanning microscope. In the confocal microscope, other than in the multi-photon microscope, remitted primary radiation and not secondary radiation is used for image formation. In the signal detection channel, the former device, other than the latter, furthermore includes a pin-hole (narrow diaphragm for eliminating remitted radiation from outside the laser focus). While because of the aforementioned particularities confocal laser scanning microscopes have a penetration depth of 50-80 µm depending on the preparation, deeper regions, e.g. down to 200 µm, in very favorable cases even down to 1000 µm, can be represented with the multi-photon microscopy, so that more meaningful pictures of living tissue, for example of skin layers of a human being, can be made.

The most widely used method for multi-photon microscopy is the two-photon fluorescence microscopy (short: two-photon microscopy). While in the conventional (single-photon) fluorescence microscopy an electron is excited in a fluorescent molecule by absorption of one photon each, i.e. is raised to a higher energy state, the excitation of the electron in the two-photon fluorescence microscopy is caused by the simultaneous or almost simultaneous absorption of two photons (two-photon absorption).

In three-photon microscopy, the excitation correspondingly is effected by three photons arriving simultaneously or almost simultaneously.

Fluorescence is obtained when dyes absorb incident (exciting) photons and subsequently again release another photon. By means of the exciting photons, an electron is raised to a higher energy level and the photon energy hence is stored temporarily. In normal fluorescence microscopy this excitation is accomplished by exactly one photon. The electron remains at the higher energy level for a few hundred picoseconds up to several nanoseconds, before it falls back again and thereby emits a new, longer-wavelength, lower-energy photon. When excitation is effected with blue light, for example, green fluorescence is obtained, as is the case with fluorescein. In two-photon microscopy, the excitation of an electron is effected by exactly two photons, which all in all have the same energy as the one excitation photon of normal fluorescence microscopy. A prerequisite for the excitation, however, consists in that the two photons arrive at the same time—within one attosecond ($10^{-18}$ s)—, since there is no stable intermediate energy level of the electron to be excited.

In normal fluorescence microscopy, the exciting photon has a shorter wavelength and hence more energy than the emitted photon. In the case of multi-photon excitation, on the other hand, excitation is effected with photons which have a distinctly greater wavelength and thus less energy per photon than the emitted photons. In this way, for example, dark-red or infrared light can be used for excitation, in order to generate green fluorescence. This is possible because two or more exciting photons lead to the generation of only one emitted photon. In the two-photon excitation, the excitation wavelength approximately is about twice the normally used excitation wavelength, in the three-photon excitation three times, etc.

The fundamental concept of two-photon fluorescence microscopy is described in the publication W. Denk, J. H. Strickler, W. W. Webb "Two-Photon Laser Scanning Fluorescence Microscopy", Science, Vol. 248, pp. 73-76 (6 Apr. 1990).

From U.S. Pat. No. 5,034,613 a device for multi-photon fluorescence microscopy is known, in which an excitation radiation generated by a laser is directed onto an object to be examined by means of movable mirrors present in the beam path. To achieve an excitation at different locations of the object and in this way form an image excited pixel by pixel, the excitation beam is changed in its position by tilting the movable mirrors such that the focus point of the excitation radiation moves through the object, excites the same location by location and thereby generates signals in the object location by location. The resulting secondary radiation (consisting of a fluorescence radiation and a possibly generated higher harmonic of the excitation radiation) is collected and detected, in order to form a complete image in one or more planes of the object with reference to the signals from the individual locations.

With the device known from U.S. Pat. No. 5,034,613 only sectional images substantially can be formed from a small segment of the object to be examined. This is due to the fact that in two-photon microscopy large apertures of the used optics are necessary because of the necessary high intensities for excitation, which require a focusing of the excitation radiation to a focus diameter of 0.5 μm up to maximally about 3 μm (this results from the laws of beam product maintenance, when optically representing laser beams). These apertures have a numerical aperture of NA=0.4 to NA=1 (or when using an immersion fluid up to NA=1.45), which corresponds to a full cone angle of the focused beam of about 50° to 135°. Such large-aperture beam bundles only can be focused by high-magnification microscope objectives or comparable complex optical systems, which inevitably only have comparatively small fields of view with a diameter of about 0.5 mm to 1 mm (field of view here is understood to be the maximum field which can be swept by a deflected excitation beam). In other words, this means: With the large apertures for focusing the excitation radiation onto the object, which are necessary for two-photon microscopy, the surface over which the excitation radiation can sweep by beam deflection necessarily is limited. By beam deflection with the use of rotary or tiltable mirrors, only fields with a diameter of maximally 1 mm can be excited, so that the recordable images are limited to edge lengths of not more than 1 mm.

To use the two-photon microscopy for example for examining a skin layer for pathological changes, such images often are too small.

Conventionally, in the two-photon microscopy a lateral scan of a plane (skin layer) initially is made and subsequently the focus depth for recording further, e.g. deeper skin layers is newly adjusted. In this way, a sequence of superimposed layers successively is recorded through the skin. From a users point of view in the case of the medical application, it would be desirable, however, to have vertical sectional images through the skin, which correspond to the cut position commonly used in histopathology, which are familiar to the medical examiners and which correspond to their diagnostic point of view.

In general, images from the skin accordingly would be desirable in a vertical cut position, which for example can fully represent a lesion extending over a length of several mm or even cm.

From EP 1 929 939 A2 an endoscopically usable device for multi-photon microscopy is known, in which the tip of an optical fiber serving as light guide with miniaturized focusing optics arranged thereon is movable in an endoscope, in order to direct an excitation radiation generated by a laser onto an object. Due to the fact that at the tip of the light guide merely an optical system of small dimension and hence also of small aperture can be used, the achievable local resolution is limited, since only comparatively large focus diameters can be achieved for local excitation. In addition, the arrangement of EP 1 929 939 A2 uses the same light guide for forwarding the excitation radiation and for returning the optical signals picked up from the object, which on the one hand places high demands on the light guide (transmission of ultra-short pulse laser radiation of high beam quality, i.e. in the TEM00 mode) and on the other hand is disadvantageous for the transmission quality and yield of the received signals. The transmitted excitation radiation additionally is deteriorated in its quality by the fiber dispersion, e.g. by enlarging the pulse duration or by the so-called "chirping". In addition, when moving the focusing optics for recording a complete image, the light guide always must be moved as well, which renders the spatial movement quite complex and at the same time limits the same, since sectional images of great lateral expansion cannot be recorded.

SUMMARY

It is the object underlying the present invention to create a device and a method for multi-photon fluorescence microscopy for obtaining information from biological tissue, which with a large field of view provide for recording in particular vertical sectional images in an object and at the same time are of simple construction and reliable in their operation. The temporal, spectral and polarization-related beam properties of the excitation radiation should not or only minimally be deteriorated on their beam path, and the handling (ergonomics) and usability should be improved.

In accordance with an exemplary embodiment of the invention it is provided that the optical unit is formed and provided to be moved in at least one direction relative to the object for generating the optical signal at different locations in or on the object.

The invention proceeds from the basic idea to use a so-called flying optic. The optical unit for focussing the excitation radiation and for exciting a secondary radiation at a location in or on the object is not firmly arranged, but is moved on the whole, in order to excite different locations of an object temporally one after the other. The local excitation thus is not effected by beam deflection by using rotary and tiltable mirrors, but by a one- or multi-dimensional movement of the optical unit as a whole. Advantageously, during the movement of the optical unit for generating the optical signal, the optical axis of the excitation radiation impinging on the object should not be changed, so that—in contrast to the use of rotary and tiltable mirrors—the excitation radiation always impinges on the object under the same angle.

Due to the fact that a beam deflection by means of rotary and tiltable mirrors is omitted, large fields of view can be achieved. This means that theoretically fields of any size can be excited, so as to form images with large edge lengths from the object to be examined. This allows, for example, to record sectional images of the human skin, which can completely represent lesions.

Preferably, the optical unit is movable in horizontal direction and/or in vertical direction relative to a surface of the object facing the optical unit. For recording a sectional image, the optical unit on the one hand is moved along the surface of the object, for example along the skin surface of a patient, wherein the movement can also be effected two-dimensionally in X- and Y-direction along the skin surface and at the same time in Z-direction vertical to the skin surface for signal generation in a three-dimensional space. In the method, different locations of the object are excited one after the other, and the secondary radiation generated in the object—consisting of fluorescence radiation generated in the object and harmonics of the excitation radiation generated by non-linear effects (SHG: second harmonic generation=generation of the first harmonic wave)—is recorded as optical signal.

To achieve a movement of the focus in vertical direction in a simple way, it can be provided to movably design not the entire optical unit (comprising for example a dichroic element for separating excitation radiation and received optical signals), but merely an objective. The objective, which for example can include an optical lens for focusing, hence is movable relative to the remaining optical unit at least in vertical direction, in order to move the focus within the object to be excited in vertical direction and generate signals in the form of a secondary radiation at different, vertically offset locations.

For generating a vertical sectional image pixel by pixel, the optical unit can at least partly be continuously movable in horizontal direction and/or in vertical direction relative to the object. The optical unit thus is moved along predefined recording lines (scan lines) and scans the object along these recording lines, wherein one after the other, for example by triggering the excitation radiation for the time-dependent exposure, locations along the recording line are excited within the object for emitting secondary radiation and signals are received from these locations. The signals of one location then provide a pixel of the image to be recorded, wherein by means of the recording lines (scan lines) the object is rastered along a plane to be observed such that a complete image is obtained, which is evaluable for example for medical diagnosis.

The device is used for multi-photon microscopy and preferably has a modular construction. As a central unit, the device includes a control and processing unit which is connected with a so-called patient module via a supporting arm. Here and in the following, "supporting arm" is understood to be a mechanical holding device which provides for a smooth and easy movability of the patient module, possibly with weight compensation, while the measuring means is positioned relative to the patient or the sample, and provides for a fixation during the time of the fluorescence imaging. The control and processing unit is of the stationary type, serves the central control of the device and the processing of the signals received and for example also includes a laser unit for generating the excitation radiation. Via the supporting arm, the patient module is movable relative to the control and processing unit and can be placed on an object to be examined such that the excitation radiation suitably falls onto the object, for example onto the skin of a patient, and signals generated can be recorded. The optical unit is part of the patient module and movable within the same, wherein the patient module advantageously includes a contact portion (for example a glass pane arranged at a housing of the patient module) transmissive to the excitation radiation and to the optical signal, which must be brought in contact with the object for examining the object. While the contact portion in one shot firmly rests against the object to be examined (for example by using an immersion fluid), the optical unit is movable in horizontal direction and/or in vertical direction relative to the contact portion and hence also to the object.

If the laser unit is part of the control and processing unit and thus spatially separate from the patient module, the excitation radiation generated by the laser unit preferably is transmitted to the patient module and to the optical unit via an optical fiber for impinging onto the object. The optical fiber can be laid to the patient module along the supporting arm or also within the supporting arm.

To achieve a simultaneous arrival of two or more photons in the focus point for the two- or multi-photon microscopy and in this way excite the molecules within the object, very high photon densities are required in the excitation radiation. The same can be achieved for example by using a pulsed laser (ultra-short pulse laser) for generating laser pulses in the femtosecond range, in particular with mode coupling. Such lasers emit very short, intensive laser pulses (with pulse lengths in the femtosecond range, e.g. 80-140 fs), which are repeated e.g. 80-120 million times per second, so that between the pulses pauses with a length of 8 to 12.5 ns (=8000000-12500000 fs) are obtained and the entire energy generated in the laser in this way is emitted in pulsed form with high intensity within a fraction of the time.

The laser unit for example can generate an excitation radiation of a first wavelength, e.g. 1560 nm. In the patient module, a frequency doubler (e.g. in the form of a frequency doubling crystal) connected before of the optical unit then can be arranged, which halves the wavelength of the excitation radiation (for example from 1560 nm to 780 nm) and hence doubles the frequency of the excitation radiation. This has the advantage that the excitation radiation can be transmitted from the laser unit to the patient module via a suitable optical fiber with a comparatively large wavelength of e.g. 1560 nm, wherein for such wavelength range fibers are available which provide for a transmission—even by maintaining the polarization ("polarization-maintaining single-mode fibers")—without significant deterioration of the beam quality. The frequency doubler then generates the first harmonic wave of the transmitted excitation radiation (e.g. 780 nm), which is used for excitation of the object.

The laser unit can also be configured as a so-called femtosecond fiber laser with led-out laser fiber, which extends up to the patient module. In this way, a so-called "pre-chirp" (a pre-distortion of the excitation radiation for compensating dispersion effects, above all group velocity dispersion, in the optical path from the laser beam source to the tissue) can be omitted, because the end of the laser fiber represents the exit point of the excitation radiation from the laser resonator and hence the primary laser radiation source. In the patient module, frequency doubling of the excitation radiation or halving of the wavelength from 1560 nm to 780 nm then is effected.

The idea to use a laser unit which generates a radiation of a first wavelength, which subsequently is converted into an excitation radiation with another wavelength and in which the primary radiation source (it generates the first wavelength) is mounted in an appliance unit and transmits its radiation via an optical fiber to a second, separate appliance unit, where the radiation is transferred into the excitation wavelength by conversion and then is further used, also represents an independent concept in this connection, which can be used in a wide variety of devices for the multi-photon fluorescence microscopy for obtaining information from biological tissue. Such device for example generally can include the following features:

a laser unit for generating an excitation radiation,
    an optical unit which is formed to focus the excitation radiation for generating an optical signal at different locations in or on an object to be examined, and
    a detector module for detecting the optical signal from the region of the object, wherein the laser unit generates a radiation of a first wavelength and transmits the same via an optical fiber to the optical unit, where it subsequently is converted into the excitation radiation with a second wavelength different from the first wavelength.

In this way, the laser unit for example can generate a radiation with a wavelength of 1560 nm, which then is converted into an excitation radiation with a halved wavelength of 780 nm and supplied to the optical unit for excitation of the object.

The concept of the linear scan by moving the optical unit along a predetermined recording line (scan line) for generating a two-dimensional sectional image or a three-dimensional volume image also is an independent inventive concept, independent of the aforementioned two-stage beam generation.

The laser beam of the excitation radiation for example can originally be polarized linearly corresponding to a transversal fundamental mode (TEM00), wherein for compensating inhomogeneities the beam can be polarized circularly before reaching the optical unit, for example be inserting a suitable quarter wave platelet.

Advantageously, the optical unit on the one hand is formed for focusing the excitation radiation onto the object and on the other hand for collecting the two-photon-excited optical signal. The optical unit can be connected with an optical fiber, via which the recorded optical signal is transmitted to the detector module for further processing. For this optical fiber (also referred to as "collection fiber"), a multimode fiber or a fiber bundle of a plurality of individual fibers preferably is used, which are joined together at their ends and thus each form a compact entry and exit surface of the fluorescence radiation.

In the detector module, which advantageously is integrated into the control and processing unit, but can also directly be inserted into the patient module, signal processing and image processing are effected. To be able to obtain both intensity information and spectroscopic information, signal processing can be effected in multi-channel form, wherein in the detector module the received signal is split up into a plurality of different signal components with different wavelength ranges, which then can be processed separate from each other. In this way, the signal is split up into different signal bands with different wavelengths, wherein the bands can suitably be chosen in dependence on the sought information. If it should be determined, for example, where a spectrum approximately has a maximum, the ratio of the spectral components in an upper band (with longer wavelengths) and in a lower band (with shorter wavelengths) can be formed. If certain fluorescent substances should be detected, a band specifically can comprise the wavelength range in which the sought substance emits a fluorescence radiation. For example, for the purpose of photodynamic diagnostics (short: PDD) or photodynamic therapy (short: PDT) porphyrins (in particular the protoporphyrin IX, PP IX) thus can be detected in cells, which upon excitation emit fluorescence radiation in certain wavelength ranges (PP IX for example at about 630 nm). From the presence of the porphyrins, the tissue condition, in particular the pathological formation of new tissue like e.g. in cancer, can be inferred, wherein this information in turn can be used for control in connection with the photodynamic therapy for the selective cell damage or destruction.

The device can be used for representing both endogenous and exogenous fluorescent substances (so-called fluorophores). Natural fluorophores occurring in human skin include for example NAD(P)H, collagen, elastin, tryptophan, flavines, lipopigments, keratin, HPD (hematoporphyrin and derivatives) as well as PP IX, which fluoresce in different wavelength ranges and hence can be detected by suitable selection of the bands each considered.

To split the received signal into signal components, the detector module includes one or more dichroic filter elements which reflect or transmit the incident radiation depending on the wavelength and hence split the same depending on the wavelength.

To be able to analyze different spectral bands in a simple way, it can be provided to exchangeably design the one or the more dichroic filter elements in the manner of a modular system. If the received signal should be observed in certain bands, the suitable set of dichroic filter elements, for example dichoric mirrors or prisms, is chosen for this purpose and inserted into the detector module. If other bands should be observed, another set of filter elements can be used and the measurement can be repeated correspondingly. This filter change can be carried out manually or in the manner of a motor-driven filter revolver or filter change magazine.

In this connection it is also conceivable to use the device for performing a high-resolution spectroscopy, i.e. to record a complete spectrum pixel by pixel. For this purpose it is required that a sufficiently large number of photons is received from each location for a sufficiently strong, evaluable signal. For this purpose, signals possibly can be integrated from a plurality of excited locations.

For detecting the different signal components, the detector module for example includes one or more detectors—depending on the number of observed bands—, which are formed for example as so-called secondary electron multipliers (Photo Multiplier Tube, PMT), as CCD line, as CCD field or as SiPMT ("Silicon Photo Multiplier", i.e. components with detector fields from avalanche photodiodes interconnected in a photosignal-additive manner) and serve the conversion of the received optical signal or its individual signal components into electronic data signals.

For image processing, the detector module is able to on the one hand generate brightness information and on the other hand spectroscopic information from the different signal components and output the same as sectional image through the object to be examined with an additional spectroscopic information and for example display the same on a monitor. From the entirety of the signal components, for example a brightness information can be derived, which supplies structural information with reference to the image contrast. Selectable and adjustable by a user, additional spectral information can be superimposed thereon, which has been obtained from the individual signal components and hence different wavelength bands. For example, the information at which locations a certain fluorescent substance is present or at which locations signal harmonic waves (e.g. SHG) occur due to structural tissue properties (for example due to the presence of collagen in certain skin layers) can be superimposed on the brightness image and be represented in false colors.

The object in addition is solved by a method for multiphoton fluorescence microscopy for obtaining information from biological tissue, in which a laser unit generates an excitation radiation, an optical unit focuses the excitation radiation for generating an optical signal at different locations in or on an object to be examined, and a detector module detects the optical signal from the region of the object. In accordance with the method it is provided that the optical unit for generating the optical signal in or on the object is moved at least in a direction relative to the object.

The advantages and aspects described above for the device can analogously be transferred to the method.

From the received optical signals, a sectional image of the object can be generated pixel by pixel at different locations of the object, wherein for an excitation pixel by pixel the object is exposed to the excitation radiation in a triggered manner. In other words, the optical unit is moved relative to the object along a suitable, previously defined recording line (scan line), and in the process the object is successively excited and hence exposed at individual locations which each exactly correspond to the location of the current focus of the optical unit, wherein triggering is controlled depending on the location and the exposure time, i.e. the time of irradiation of a certain location, can be adjusted in a suitable way.

Triggering the excitation radiation among other things serves for defining the pixel size. The pixel size of the image obtained from the received, location-dependent signals is determined in horizontal direction by the focus width of the excitation radiation and by the triggering adjustment, whereas in vertical direction the pixel size is given by the waist length of the focused excitation radiation. The pixel size then is adjustable by a beam expansion of the excitation radiation and by adjusting the triggering, wherein for example for spectroscopy comparatively large pixels can be used, in order to obtain a signal of comparatively strong intensity, whereas for high-resolution microscopy preferably small pixels are used. The image formation (microscopy) and the spectroscopy can proceed in parallel during the same scan operation.

In this connection it is conceivable to adjust the pixel size in steps or steplessly, in that on the one hand the beam expansion is switched over by means of a change of magnification or a ZOOM in an expansion telescope and thereby the waist length and hence the vertical extension of the pixel is adjusted, and on the other hand the lateral extension of the focus is varied correspondingly by switching over the triggering.

In the two-photon microscopy, the excitation radiation is focused into the object (in general a tissue) as described above in the form of a laser beam with a high aperture, in order to achieve a small focus diameter and a low depth of field and hence a small fluorescence excitation volume, i.e. a high lateral and axial local resolution. Turning away from this, a so-called "homogenized fluorescence excitation" can alternatively be used, which has the objective to excite a laterally limited, but axially (vertically) expanded region of the object such that in axial direction object layers largely equally contribute to the optical signal at least over a certain depth range. This optical signal then is recorded and integrated and can be evaluated and be processed further as an individual measured value, as spectrum or in multi-channel form with separate spectral bands ("band spectroscopy").

For recording purposes, the optical unit is moved exclusively in horizontal (lateral) direction (in X- or in X- and Y-direction) relative to the surface of the object and the optical signal is integrated in vertical direction. There is obtained a measured value field which does not represent an object image (tissue image) like in the conventional two-photon microscopy, but supplies a laterally locally resolved information on the object condition on the whole.

The homogenized fluorescence excitation can be achieved in that the excitation radiation is radiated into the tissue with a comparatively small aperture and is focused on a certain depth. The excitation beam focused by an objective of the optical unit, for example an aspherical lens, here is defined by the aperture, the focus depth and the focus diameter. For the homogenized fluorescence excitation, the focus depth advantageously is adjusted to a value between 100 µm and 450 µm, preferably 200 µm to 350 µm (measured in air, before placing the measurement system onto the skin, i.e. without correction of the tissue refractive index), the focus diameter is adjusted to a value between 6 µm and 10 µm, preferably between 7 µm and 9 µm, and the aperture is adjusted to a value between 50 and 80 mrad (corresponding to the sine of half the opening angle of the aperture cone in air, i.e. without correction of the tissue refractive index).

Surprisingly, it was found that by this adjustment of the parameters for the homogenized fluorescence excitation undesired effects can be compensated and balanced. Normally, the excitation radiation in a tissue is attenuated by scattering and absorption, so that tissue regions in a greater depth are excited to fluoresce less than regions close to the surface. In addition, the optical signal from regions close to the surface is attenuated less on its way from the place of excitation to the measuring system than optical signals from greater depths. Both leads to the fact that the measured optical signal normally is determined very predominantly by the regions close to the surface (for skin this means for example that the keratin layer, which is greatly influenced by foreign substances such as cosmetics and anyway can be observed well from outside, outshines the desired optical signal from the depth). With the chosen parameters for adjusting the focus depth and width as well as the aperture, the excitation probability increases to an extent in which the aforementioned depth effects attenuate the optical signals, due to the two-photon excitation in which the excitation probability increases in proportion to the square of the intensity. Thus, a generally largely balanced contribution of all tissue layers to the measured optical signal is obtained.

The integration depth for the optical signal in the object (tissue) largely is limited by the fact that after reaching the focus depth the two-photon effect no longer is effective. By means of optical measures such as providing a diaphragm in the collection optics (collection efficiency limitation), this cut-off effect can even be amplified.

As a further advantage it is found that fluctuations of the focus depth with otherwise constant parameters of the focused excitation radiation influence the measured optical signal (integrated over the depth) to an only small extent. The measurement thus is comparatively insensitive to fluctuations of the coupling of the measurement system to the skin.

At this point is should be noted that the principle both of the flying optics and of the homogenized fluorescence excitation can advantageously also be applied to the confocal microscopy and the confocal (single-photon) fluorescence microscopy by a suitable choice of diaphragms and focusing.

BRIEF DESCRIPTION OF THE DRAWINGS

The idea underlying the invention will be explained in detail below with reference to the exemplary embodiments illustrated in the Figures.

DETAILED DESCRIPTION

Figure 1:
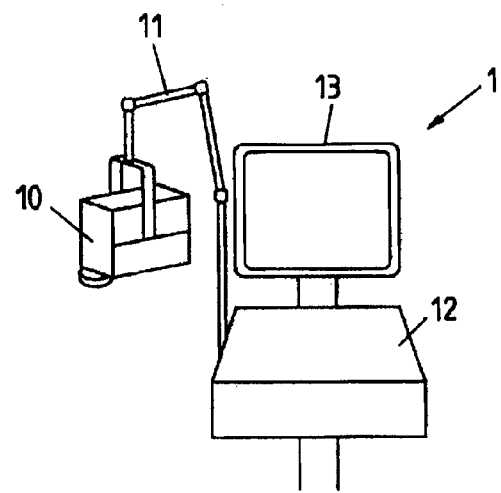
FIG. 1 shows an overview representation of a device for multi-photon fluorescence microscopy, including a central control and processing unit which via a supporting arm is connected with a patient module to be arranged at a patient.

FIG. 1 shows an overview representation of a device 1 for multi-photon fluorescence microscopy for obtaining information from biological tissue, which includes a control and processing unit 12 which is connected with a so-called patient module 10 via a supporting arm 11. While the control and processing unit 12 as a central, stationary unit on the one hand performs the control of the device and on the other hand the processing of the received signals and outputs results in a suitable way via a monitor 13, the patient module 10 is formed as a module adaptable in its position and arrangeable at a patient, which chiefly includes optical components for conditioning, transmitting and optically modifying an incident excitation radiation generated by a laser unit of the control and processing unit 12 and transmitted to the patient module 10 via an optical fiber on the one hand and for recording a received optical signal on the other hand.

The patient module 10 thus represents a measuring head which is freely movable and precisely lockable via the multiaxial supporting arm 11, so that after exactly positioning the patient module 10 relative to a patient, pictures with a microscopic resolution can be made. Via fiber-optic and electric connections, the patient module 10 is flexibly connected with the control and processing unit 12.

For positioning the patient module 10, a foot switch can be provided for controlling a motor-driven movement of the supporting arm 11.

The device 1 advantageously is designed vibration-damped by minimizing the moving mass. To avoid external interfering radiation, the housing of the patient module 10 must be light-tight.

The control and processing unit 12 also includes a control PC, via which user input and output devices (mouse, keyboard, joystick, monitor) can be connected.

The device 1 can functionally be divided into
- an optical system, consisting for example of an objective, beam shaping and collection optics, a number of optical detectors for example in the form of so-called Photo Multiplier Tubes (PMTs), associated dichroic filter elements and filters, quartz fibers for light transmission, an ultra-short pulse laser, a beam attenuator in the form of a polarizer, an exposure device for controlling the laser exposure, and a real image camera with associated lighting system,
- a mechanical system, consisting for example of the supporting arm 11, piezoelectric linear motors with control units and associated table system, a stepper motor for the beam attenuator, an optic changer for the motor-driven and manual change between microscopy optics and real image camera, and a patient adapter for fixing the optics at the patient,
- a signal-processing system, consisting for example of amplifiers, an electronic unit for converting and evaluating the received signals and for data storage, photodiodes for power control and ambient light monitoring, and associated converters, as well as
- a data-processing system, consisting for example of a graphical user interface with data management functions and an electronic control system which coordinates all functions of the optical, the mechanical and the signal-processing system.

The device 1 is formed for the multi-photon fluorescence microscopy, in particular for the two-photon microscopy. The device 1 should serve as a non-invasive system for the diagnostic assistance of a physician, which by utilizing two-photon processes in particular in vivo supplies cross-sectional images of the human skin with additional spectral information, due to which a physician obtains additional information supporting his diagnostic decision, as compared to a pure surface image.

In principle, the device 1 can be utilized for applications supporting the diagnosis of all degenerations of the skin, which are reflected in structural changes of the tissue. The device 1 is able to
- provide image-forming depth information with microscopic resolution from epidermal/dermal skin layers,
- generate sagittal sectional representations of the skin corresponding to the histopathological thin sections,
- provide spectral information in the sense of a locally resolved wavelength band spectroscopy by using different spectral channels, and
- supply functions supporting the diagnosis, e.g. mechanical evaluation aids.

The device 1 is suitable for patients of any age with skin lesions which are diagnosed not only by clinical assessment, but for example should undergo biopsy. By using the device 1, an (invasive) biopsy possibly can be avoided, or a targeted preselection for biopsies can be made. Lesions in question in particular include skin areas with suspected Morbus Bowen, basal cell carcinoma, squamous epithelial carcinoma or actinic keratosis. The operation of the device is effected by trained personnel which provides and possibly prepares the image material for the attending physician, or by the physician himself.

Figure 2:
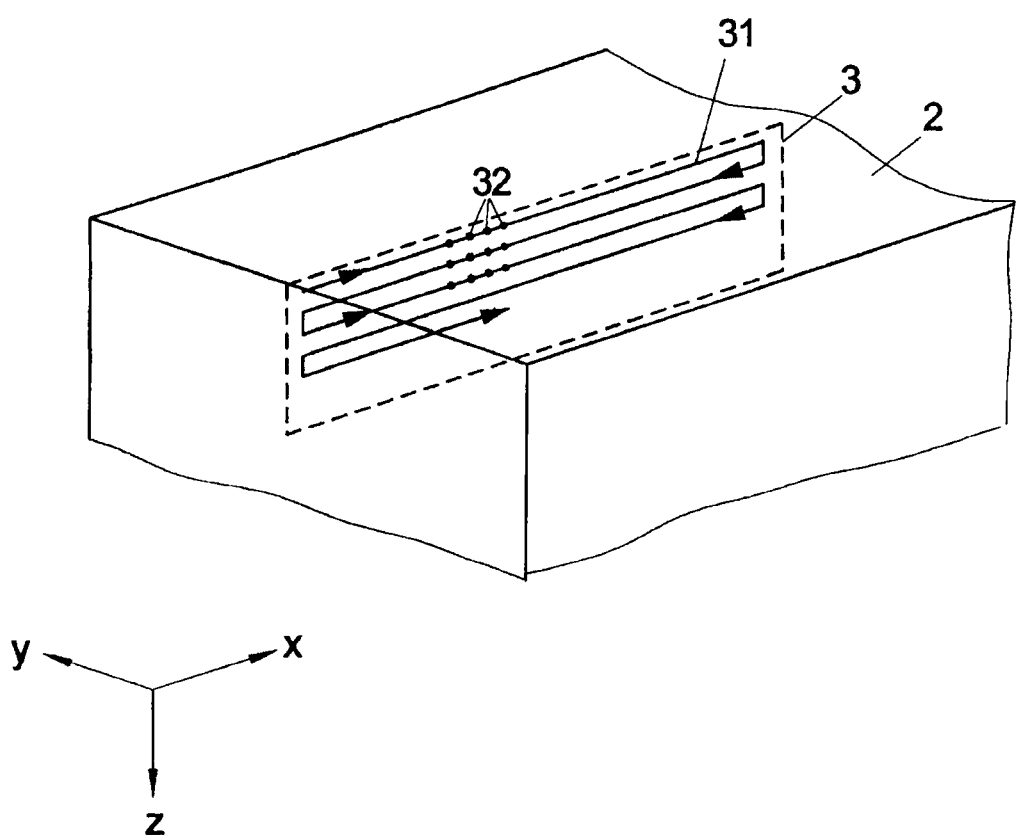
FIG. 2 shows a schematic representation of a vertical (sagittal) sectional image.

With the device 1, in particular vertical (sagittal) sectional images can be taken through the skin of a patient. As is schematically shown in FIG. 2, this is done in that in connection with the two-photon microscopy the skin tissue is excited at individual locations 32 in a sagittal image plane 3 along a recording line 31. The excited location 32 each corresponds to a region around the focus point of an excitation radiation with an extension in X-direction (horizontally) of e.g. 0.5 µm and in Z-direction (vertically) of e.g. 2 µm, and is selected by shifting the focus point along the recording line 31.

Figure 3:
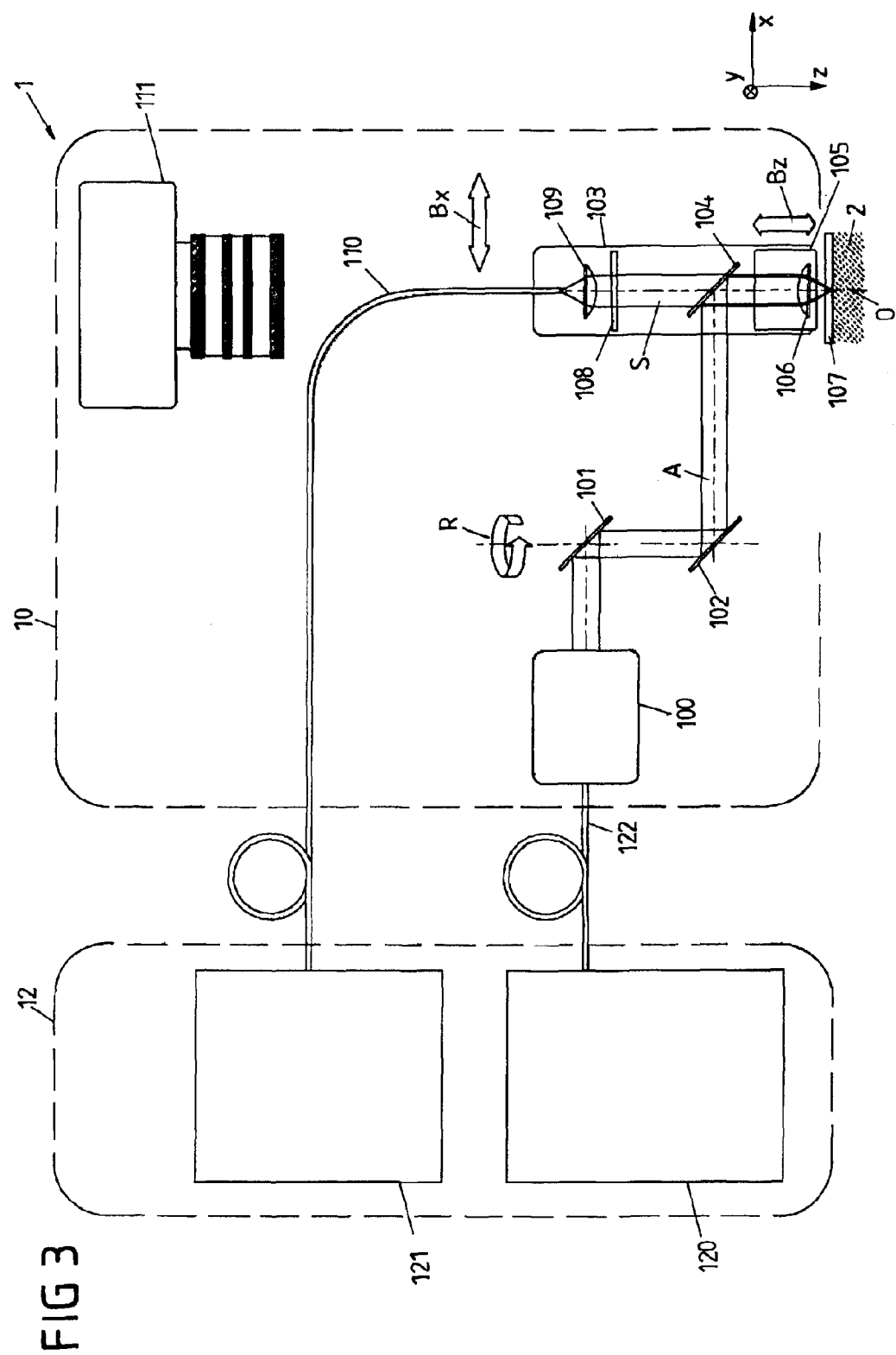
FIG. 3 shows a schematic overview of a device for multi-photon fluorescence microscopy with its individual components.
Figure 4:
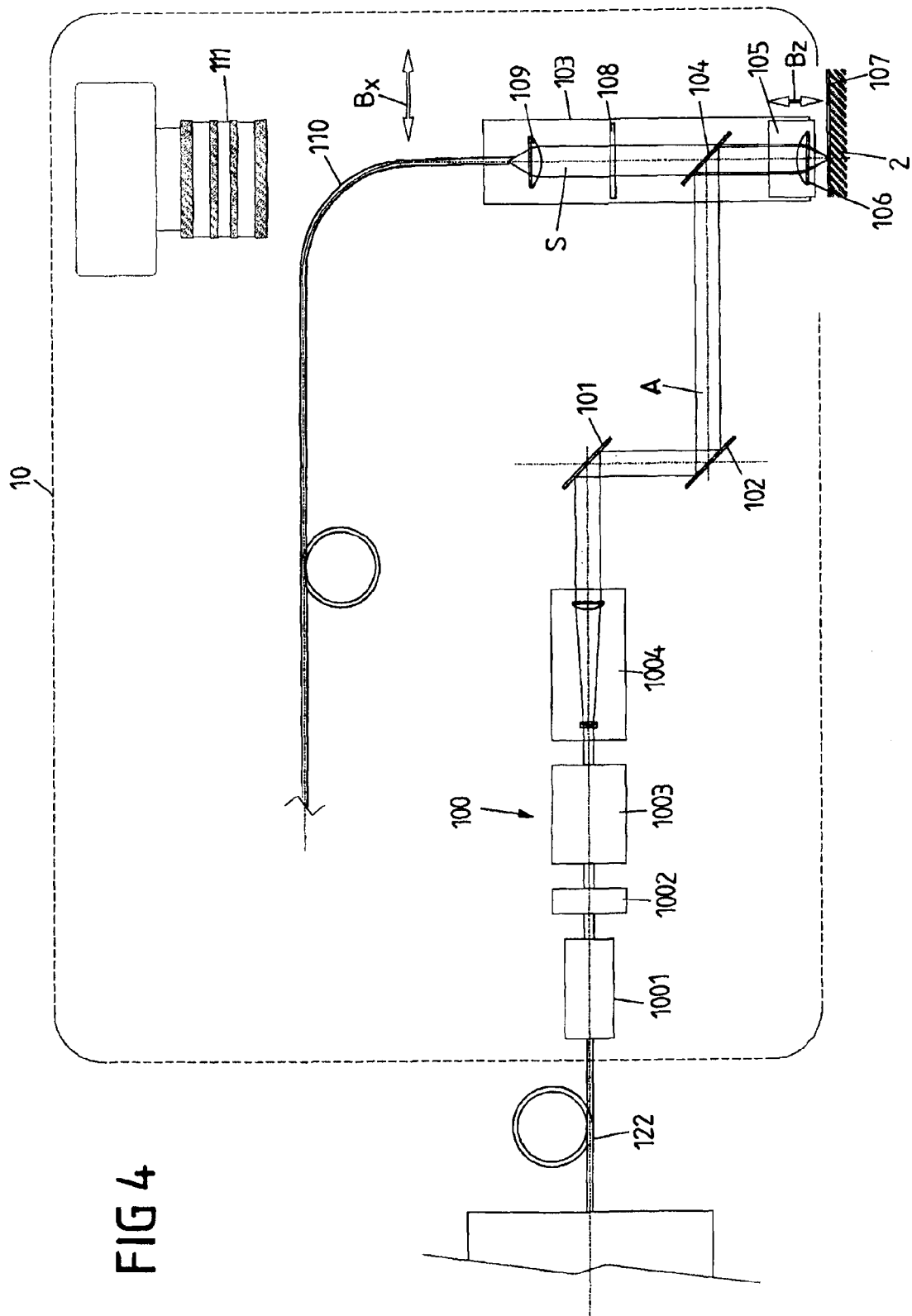
FIG. 4 shows a schematic view of a patient module.
Figure 5:
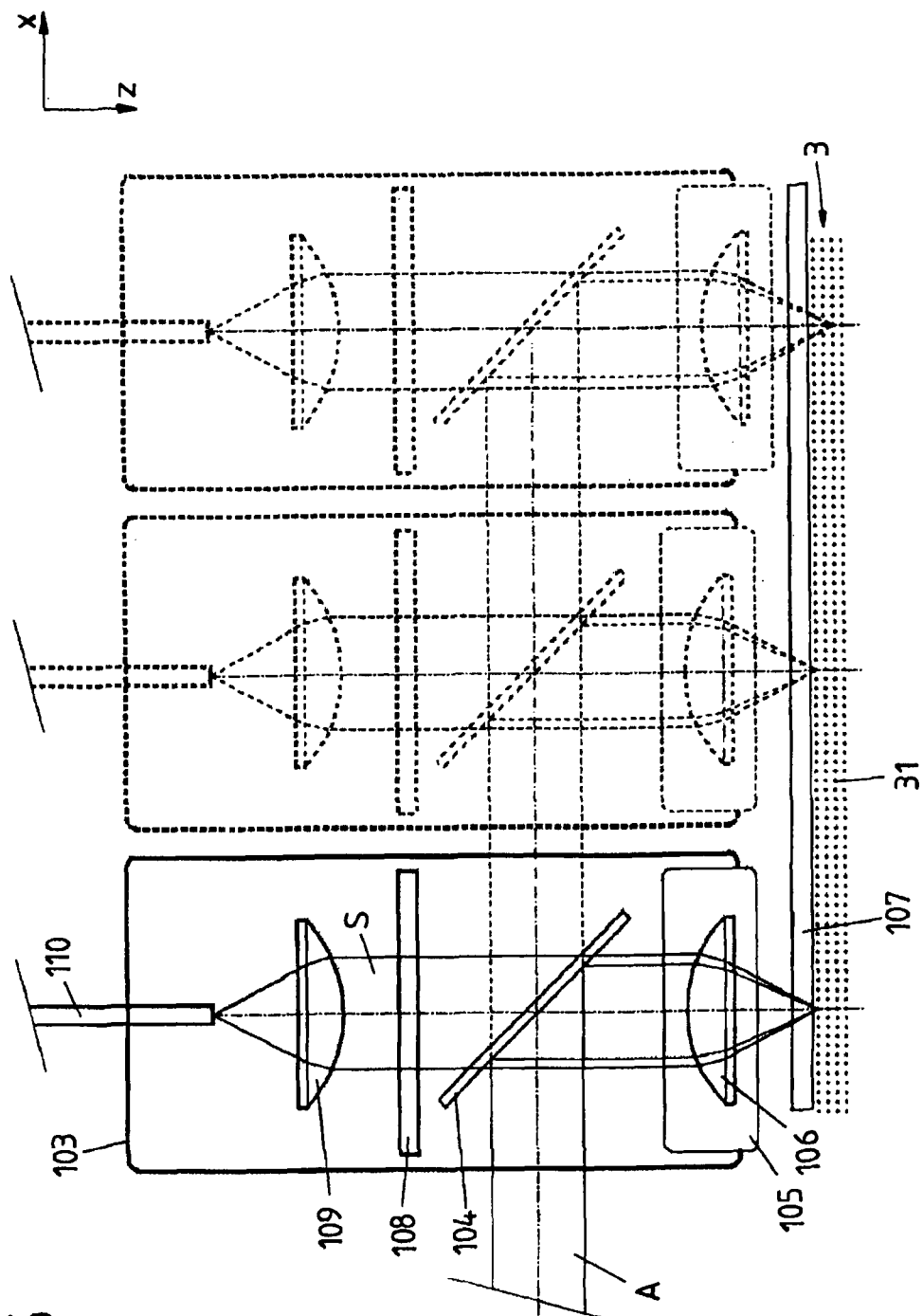
FIG. 5 shows a schematic view of a horizontally and vertically movable optical unit of the patient module for recording a sectional image.

In the device 1, shifting the focus point is achieved by an optical unit 103 of the patient module 10 which is movable in at least two directions, as is shown in FIGS. 3 to 5 and will be explained below.

FIG. 3 shows a schematic overview representation of an embodiment of the optical system of the device 1, and FIG. 4 shows a schematic view of the optical setup of the patient module 10.

The optical system substantially consists of a compact two-photon microscope which includes a laser unit in the form of an ultra-short pulse laser 120 (fs fiber laser), a detection system in the form of a detector module 121, and a real image camera 111 with lighting for recording a real image.

For two-photon microscopy, the ultra-short pulse laser 120 arranged in or at the control and processing unit 12 generates an excitation radiation A with a fundamental wavelength of 1560 nm+/−10 nm, which is supplied to the patient module 10 via an optical fiber 122 in the form of a single-mode fiber.

In the patient module 10, the excitation radiation A initially is supplied to a device for beam conditioning 100, in whose frame, as is shown in FIG. 4, the wavelength of the excitation radiation A is halved to 780 nm by a frequency doubler 1001 in the form of a suitable crystal (i.e. the frequency is doubled). Subsequently, the excitation radiation A passes through a filter 1002 which filters out the fundamental wavelength (1560 nm), the third harmonic (520 nm) and the fourth harmonic (390 nm) and hence merely lets pass the frequency-doubled excitation radiation A with a wavelength of 780 nm. In a power setting and measuring device 1003, the beam power is controlled, wherein for example an attenuator can be provided for attenuating the excitation radiation power. The attenuator serves the reduction of the laser power after frequency doubling from a value of for example about 100 mW to a value of 0% to 100% of the allowed emission power (corresponding to the power radiated by the optics onto the object 2, for example max. 50 mW) at the location of the two-photon excitation. The attenuator is precisely and reproducibly adjustable via a motor, wherein the motor for example is controllable via a user interface. By means of an optical measurement (for example via a PIN photodiode), the actual power after the attenuator is monitored.

Finally, the excitation radiation A passes through a telescope 1004, which expands the laser beam and shapes the same in a suitable way.

The characteristics of the ultra-short pulse laser 120 for example can be as follows:
fundamental wavelength: 1560 nm+/−50 nm;
wavelength after frequency doubling: 780 nm+/−30 nm;
spectral width (780 nm): 8.8 nm;
beam diameter (780 nm): 1.3 mm;
beam divergence (780 nm): 3.8 mrad;
M2 (780 nm): 1.07;
pulse repetition frequency: 100 MHz;
pulse duration (780 nm): <150 fs;
mean power (780 nm): >100 mW.

In an alternative solution, the excitation radiation A (with a wavelength of 780 nm) can also be generated directly in the control and processing unit 12 and be transmitted to the patient module 10 via a suitable optical fiber 122, in particular a so-called Photonic Fiber.

Instead of a fiber 122, there can also be used a mirror joint arm for the flexible transmission.

In a further alternative solution, the two-photon excitation radiation A can be generated directly in the patient module 10, in which a laser then is integrated. An optical fiber for transmitting the excitation radiation A from the control and processing unit 12 to the patient module 10 then can be omitted.

As radiation source, a laser in the form of a femtosecond laser, such as a titanium-sapphire laser, can also be used in all cases, which (instead of the radiation at 1560 nm for generating the excitation radiation at 780 nm) generates an excitation radiation in the range from 700 to 900 nm, which then is directly used for excitation without frequency doubling.

After beam conditioning, the excitation radiation A is directed via mirrors 101, 102 to the optical unit 103, deflected to an objective 105 via a dichroic mirror 104, focused by an aspherical lens 106 and radiated onto an object 2, for example the skin of a patient.

The patient module 10 includes a contact portion 107 in the form of a glass pane transmissive to the excitation radiation A, which is firmly in contact with the skin for example by using an immersion fluid for improving the microscopic resolution.

For adjusting the location of the focus, the optical unit 103 is adjustable. For lateral movement of the focus point relative to the contact portion 107, the optical unit 103 is movable at least in X-direction (corresponding to a lateral movement BX), advantageously also in Y-direction, i.e. two-dimensionally along the surface of the object 2. At the same time, the objective 105 of the optical unit 103 is adjustable in Z-direction (corresponding to an axial movement BZ), so as to also vertically move the focus point in Z-direction (alternatively it is also conceivable to design the entire optical unit 103 movable in Z-direction). By moving the focus point within the object 2, sectional images can be generated, wherein the lateral movability of the optical unit 103 provides for generating sectional images with large lateral edge lengths of for example several mm or also cm.

FIG. 5 schematically shows the movement of the optical unit 103 during the recording process of a vertical (sagittal) sectional image. For recording signals at different, laterally offset locations 32, the optical unit is moved along the recording line 31 (see FIG. 2) initially continuously along the X-direction and hence horizontally relative to the object 2 (and the contact portion 107 in the form of a glass pane of the patient module 10 firmly arranged at the object 2). During the movement of the optical unit 103, different locations 32 are excited by a location-dependent triggered exposure to the excitation radiation A, and the excited signal is recorded. In this way, a number of image points (for example several hundred or also thousand) are recorded in a line. When the end of a line is reached, the objective 105 of the optical unit 103 is shifted in Z-direction and hence the focus is moved in Z-direction. The optical unit 103 then is moved back along the X-direction, the next line is recorded and so on, until finally the entire image has been recorded.

This sequence of scanning (first laterally, then into the depth) can of course also be accomplished in reverse order (first into the depth, then laterally).

The surface-normal scanning ("Z-scanning") can be accomplished by a vertically oscillating suspension of the objective 105, which is periodically excited or driven and thus carries out the Z-movement. For the oscillating suspension in particular leaf springs, leaf spring joints, annular springs or air springs can be used, which are driven piezoelectrically, electromagnetically or power-operated via a mechanical cam gear or eccentric gear. The lateral movement of the optical unit 103 then is effected continuously in only one pass per sectional image, i.e. correspondingly slower. The advantage of this arrangement consists in that the objective 105 has a distinctly lower mass than the optical unit 103 as a whole, therefore can be moved fast with lower mass forces, and thus generates less vibrations of the device 1.

Furthermore, scanning can be effected not only two-dimensionally ("2D"), but also three-dimensionally ("3D"), by performing two lateral scans (X and Y) and one depth scan (Z) one after the other in any order.

The movable optical unit 103 of the patient module 10 provides for a motorized movement of the imaging optics over the object 2, wherein the direction (0°-180°), lateral position and lateral length can be chosen freely by the user. The movement of the optical unit 103 in the plane parallel to the object surface for example can be effected by two piezoelectric linear motors which are moved in a mechanically coupled and coordinated way. As an alternative to a coordinated motor movement, it is also possible that only one linear motor is provided for a one-dimensional movement along the skin surface, wherein for defining the scan direction the entire patient module 10 along with the optical unit 103 is manually rotated and aligned by the user, in order to determine the scan direction.

One of the lateral movements also can be effected as a rotary movement (in the sense of a rasterization in polar coordinates) about the axis of rotation R shown in FIG. 3. A first motor then moves the optical unit 103 linearly (in radial direction), while a second motor rotates the optical unit 103 about the axis of rotation R.

The resolution of the recorded image is determined by the size of its image points (pixels). In the case of the two-photon fluorescence, the same are defined by the focus size of the excitation radiation A, wherein advantageously a focus size of 0.5 μm in lateral direction (X direction) and 2 μm in axial direction (Z-direction) is used, in order to achieve a cellular resolution. To keep the mass of the optical unit 103 to be moved as small as possible, an individual aspherical lens 106 is used for focusing, which is possible due to the fact that the optical axis O of the excitation radiation A radiated onto the object 2 is not changed in its angular position when recording an image (in contrast for example to the use of rotary and tiltable mirrors) and therefore optimum focusing properties only are required in the direct vicinity of the optical axis O. The aspherical lens 106 for example can have a geometrical-optical focal length of f=8 mm, a working distance (defined as focus-side intersection length, i.e. the distance of the focus point from the nearest optical surface of the lens) of 6 mm and a numerical aperture of NA=0.55.

By means of the excitation radiation A, secondary radiation is excited in the object 2 at individual locations corresponding to the focus point of the excitation radiation A. The secondary radiation on the one hand can consist of a fluorescence radiation, generated by endogenous and exogenous substances, and on the other hand of harmonic waves generated on structures in the object, in particular the second harmonic (SHG: second harmonic generation). The secondary radiation is recorded by the optical unit 103 as signal S and coupled into a second optical fiber 110 via the lens 106, the dichroic mirror 104, a barrier filter 108 for suppressing the excitation radiation A and a lens 109, and transmitted to the detector module 121 of the control and processing unit 12. The lenses 106 and 109 preferably can be designed as asphere, but alternatively also independently be selected as spherical single lens or lens group (e.g. as achromat or microscope objective) or as imaging mirror arrangement.

Figure 6:
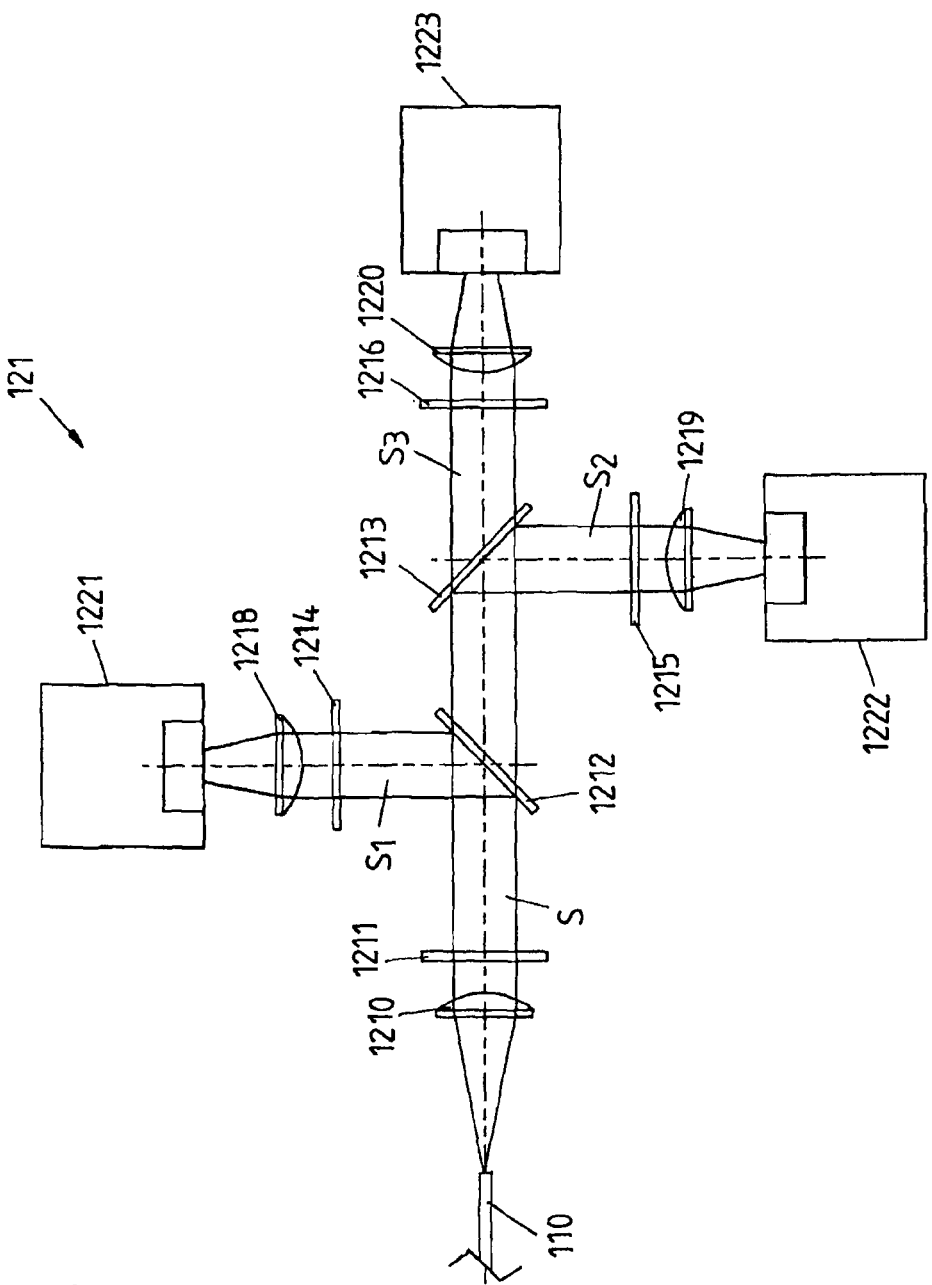
FIG. 6 shows a schematic view of a detector module for detecting received signals.

The received signals are transmitted to the detector module 121 of the control and processing unit 12 (see FIG. 3). A detailed view of an embodiment of the optical design of the detector module 121 is shown in FIG. 6. The detector module 121 has a three-channel design and includes three detectors in the form of secondary electron multipliers 1221, 1222, 1223 (Photo Multiplier Tube, PMT). The signal S supplied to the detector module 121 via the optical fiber 110 is bundled by an aspherical lens 1210, guided through a barrier filter 1211 in the form of a short-pass filter for the further suppression of reflected or scattered excitation radiation A, by dichroic filter elements 1212, 1213 split into three signal components S1, S2, S3 in different wavelength bands, and supplied to the detectors 1221, 1222, 1223 via barrier filters 1214, 1215, 1216 and lenses 1218, 1219, 1220.

With a four- or multi-channel design, it is also possible to provide more filters, lenses and detectors corresponding to the number of channels.

As detectors 1221, 1222, 1223, PMTs with suitable spectral sensitivity (photocathodes) are used, which via the dichroic filter elements 1212, 1213 serving as beam splitters obtain sub-bands of the visible spectrum from the fluorescence light supplied via the fiber 110. The entire system is disposed in a completely light-tight and internally blackened housing, in order to suppress disturbing reflections and stray light. The electrical signals generated by the PMTs initially are amplified—wherein the amplifiers should be arranged in the surroundings of the PMTs, in order to minimize electromagnetic intereferences—and then digitized.

As measurement quantity for the detection, the charges per pixel from the different channels are used, which are obtained per detector 1221, 1222, 1223 from the integration of the photocurrent over a pixel integration time. A fluorescence image is created from these signals by means of suitable parameters (e.g. calibration values per channel, brightness and contrast correction, false color function and the like). For this purpose, the charges are converted into a voltage at a specifiable pixel rate, e.g. by integration of a current through the detectors 1221, 1222, 1223, and this voltage is digitized with e.g. 12 bit.

With incident light, PMTs generate small currents in the range from nA to μA, which must be further processed correspondingly. After each PMT a current amplifier is connected, which for example has a band width of 200 kHz to 8 MHz, an amplification factor $\leq 10^5$ and an input impedance equal to the impedance of the PMT (50 Ohm), and which is designed stable to drift and of low noise. After each amplifier an integration circuit is connected, which is triggered externally (by an encoder clock which is derived from the moving optics) and converts the current signal of the associated PMTs into a voltage value. By means of an analog-to-digital converter, this voltage is converted into a 12-bit value and stored in a buffer memory, from which the data are sent to a computer interface for further processing.

At low signal photon flow rates, the PMTs or SiPMTs can alternatively also be used in the single photon counting operation. As digital output signals, one registered event number, the "photon count", each is obtained in this case per pixel and channel.

When recording a microscopy sectional image, the optical unit 103 (see FIG. 3 and FIG. 5) is continuously moved along the X-direction with a constant linear velocity. The measuring rate is determined by a locally activated trigger, namely the encoder clock of the linear motor. Since the measurement should be made with microscopic accuracy (resolution<1 μm), the requirements concerning the accuracy of the rasterization are high for the moving optical unit 103. If the integration process of the detectors 1221, 1222, 1223 is controlled by the encoder clock of the linear motor, fluctuations of the speed of movement do not result in image distortions, wherein deviations in the starting and end positions of the individual lines should not exceed the width of a pixel, i.e. for example 0.5 μm. The integration for all channels must occur at exactly the same time, in order to obtain locally identical data in the individual channels.

For controlling the exposure of the object to the excitation radiation, a so-called shutter is used, which constitutes an opaque element and is moved into the beam path of the excitation radiation for shielding off and interrupting the excitation radiation. The shutter only is opened during a shot and is closed in particular during the system check, in the case of an emergency shut-off, in the case of missing patient contact, as long as no shot is made, and in the reversal points of a recording line for minimizing the laser radiation into the skin of the patient. The shutter can be controlled by a control software, wherein in case of a malfunction an automatic and software-independent closure can be provided. For exposure of the individual locations of the object, in order to generate the individual pixel signals, the shutter is switched with a comparatively high clock rate (in the region of few ms) during a shot, wherein possibly a main shutter and a measurement shutter can be provided, of which the main shutter always is open during a shot and the measurement shutter is switched upon activation by the trigger.

In the design as shown in FIG. 6, three channels are provided for detecting three spectral bands. The same include:
- an SHG channel in a wavelength band of 390 nm±5 nm,
- a first short-wave channel in a wavelength band of 450 nm±50 nm, and
- a second short-wave channel in a wavelength band of 550 nm±50 nm.

The SHG channel should exclusively detect the narrow-band, non-resonantly generated tissue SHG, while the two short-wave channels detect the auto-fluorescence signal with the possibility to determine a locally resolved spectral ratio formation.

In an extended design, a fourth channel additionally can be provided in a wavelength band of 625 nm±25 nm, which is intended to detect fluorescence signals which are caused by markers such as PP IX or ALA.

Figure 7:
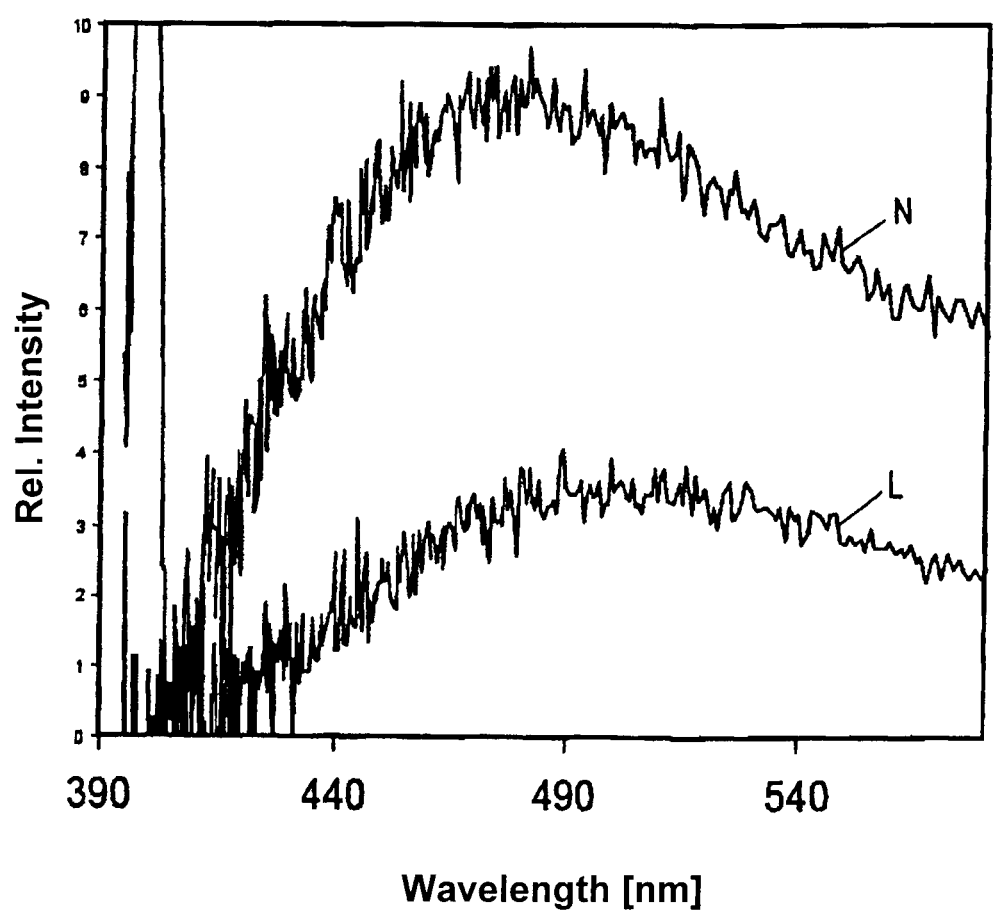
FIG. 7 shows a graphical representation of two exemplary spectra.

Two exemplary spectra are shown in FIG. 7, one for a spectrum N from a normal skin and one for a spectrum L from a lesion, i.e. a pathologically changed skin. What is distinctly visible in the two spectra L, N for example is a signal peak around 390 nm, caused by the generation of the second harmonic (SHG), and a spectral characteristic with a pronounced maximum at about 480 nm (N) and 500 nm (L), respectively.

The signal peak at 390 nm can be recorded by the SHG channel, while the position of the maximum in a spectrum L, N can be inferred by ratio formation of the signals of the two short-wave channels.

Figure 8:
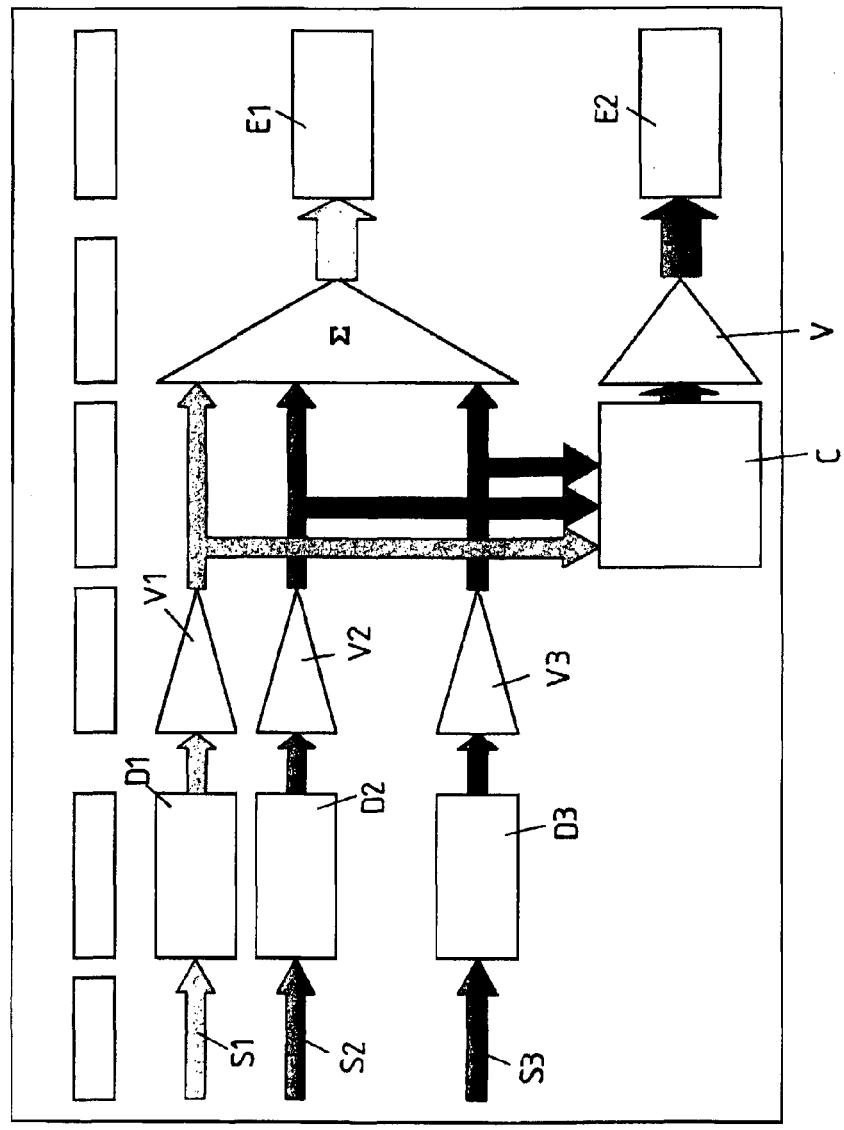
FIG. 8 shows a diagrammatic representation of a method for signal processing.

FIG. 8 shows a processing scheme of different signal components S1, S2, S3 with a multi-channel configuration of the detector module 121. The different signal components S1, S2, S2 each are detected by a detector D1, D2, D3 (for example a PMT, cf. FIG. 6) and converted into one electronic data signal each, which subsequently is amplified by amplifiers V1, V2, V3. The electronic signals thus obtained now can be processed further for obtaining information. For example, by forming a sum Σ, the signal components S1, S2, S3 can be combined to a complete signal from which a brightness information is obtained. The result image E1 for example can be displayed on a monitor as black-and-white image and can tell a user what signal intensity distribution is obtained in the tissue observed. At the same time, the individual signal components S1, S2, S3 can also be processed separately after the amplification, in order to generate result images E2 which for example provide information on the presence of a fluorophore at certain locations in the tissue and can be superimposed on the brightness image E1 in false colors. There is obtained an image in which the brightness information is displayed in black and white and additional spectral information from the individual signal bands is displayed in false colors.

Said combined image information (result images E1, E2, etc.) analogously can be generated from the signals S1, S2, etc., as shown. Alternatively, analog-to-digital conversion also can be effected right after the amplifiers V1, V2, etc., in order to subsequently obtain said result images E1, E2 by digital signal processing or calculation.

Different signals from the different bands can be superimposed on the brightness image E1 in different colors. For example, the signal corresponding to the PP IX can be displayed in red and the signal corresponding to the second harmonic (SHG) can be displayed in blue, wherein it can be provided that for the problem-related optimization of the representation and for representing specific diagnostic information by means of an input instrument such as a joystick, a slide control or possibly by means of voice control, the user can adjust the signal level of the individual signals for superposition.

Possibly, there can also be performed a logarithmic brightness correction or an automatic contrast optimization.

Figure 9:
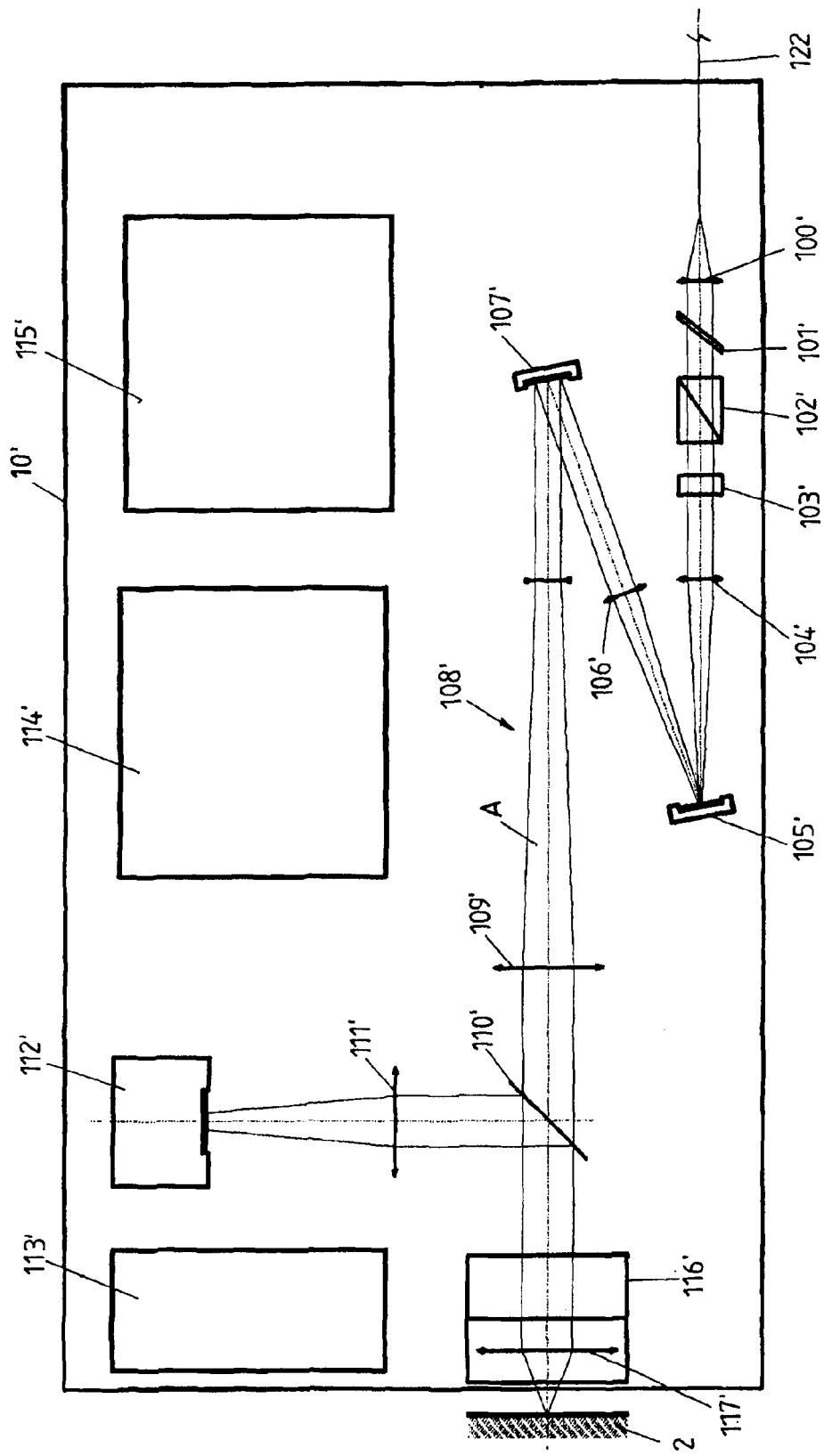
FIG. 9 shows a representation of an alternative embodiment of a patient module

FIG. 9 shows a configuration of a patient module 10', in which a biaxial tiltable mirror 107' is used for adjusting the focus point of the excitation radiation A and hence the location of the excitation. The excitation radiation A supplied via the optical fiber 122 initially is collimated by a lens 100', halved in its wavelength (for example from 1560 nm to 780 nm) by a frequency doubler 101', circularly polarized by a polarizer 102' and a quarter wave platelet 103' (the excitation radiation A transmitted by the optical fiber 11 originally is polarized linearly), directed onto a first adaptive mirror 105' by a lens 104' and directed from said mirror via a lens 106' onto the biaxial tiltable mirror 107'.

The mirrors 105', 107' for example can be manufactured as MEMS components (MEMS: micro-electromechanical systems). The first mirror 105' serves for varying the wave front, while the second mirror 107' deflects the excitation radiation A by biaxial tilting for spatially moving the focus point.

By means of a telescope for beam expansion 108', a lens 109', a dichroic beam splitter 110', an objective 116' with an aspherical lens 117' the excitation radiation A thus deflected is directed onto an object 2, for example the skin of a patient, and excites the tissue to emit a secondary radiation which in turn is passed through the objective 116' and the beam splitter 110' via a lens 111' towards a detector 112', which receives the secondary radiation as optical signal and converts it into electronic data signals.

For evaluating the data signals and for controlling the individual assemblies, the patient module 10' includes driver electronics 113' (in particular for controlling a vertical movement of the objective 116'), detector electronics 114' for controlling the detector 112' and for further processing the received signals, and control electronics 115' for adjusting the mirrors 105', 107'.

In all exemplary embodiments of the device 1 as described above, the focus of the two-photon excitation radiation A can quickly be moved ("wobbled") by a small deflection about its center position by suitable means as an additional measure, so that the fluorescence excitation can be averaged over a suitable volume during the recording time (=integration time). The recording volume ("integration volume") thus obtained, from which the two-photon-excited signals S originate, is larger than the volume corresponding to the focus point and provides an evaluable signal strong enough for spectroscopy. Beside a homogenization of the signal S, the purpose thus is achieved that the sample or the examined tissue is not unnecessarily loaded by an extensive irradiation of the same microscopic focus volume.

In a particularly advantageous way, this micro-movement of the focus can be carried out in such a way that the excitation volumes, i.e. those regions of the foci whose intensity is sufficient for the multi-photon excitation, of laser pulses directly succeeding each other do not overlap. The advantage of such a procedure consists in that the risk of an optical damage of tissue is reduced significantly. In the case of an overlap, the subsequent pulse impinges on tissue regions already optically excited by the preceding pulse. Since in the ultra-short pulse lasers used the pulse interval lies in the order of magnitude of 10 ns, i.e. in the order of magnitude of the fluorescence decay times, there exists a non-negligeable probability for transforming primarily excited molecules in the tissue into an even higher energy state, which then leads to permanent changes of the molecules.

For the fast micro-movement ("wobbling") of the excitation radiation A for two-photon spectroscopy, for example an oscillating or rotating optical component, e.g. a lens, a mirror, a prism or the like can be used.

An advantageous embodiment represents a wobbling mirror, i.e. a mirror which is mounted on an axis of rotation driven by a motor for a fast rotary movement such that between the axis of rotation and the mirror normal a small angle (for example 0.5° to 2.5°) exists. Accordingly, the reflected beam rotates about its axis at a fast rate, which leads to a small circular movement of the focus and hence to a focus movement free from overlap.

A further advantageous embodiment is a mirror oscillating in two axes, in particular a MEMS, in which the oscillation frequencies of the two main oscillation axes lying vertical to each other are in a relation to each other which corresponds to a rational number as fraction of two prime numbers. If this biaxial oscillation of the mirror is excited by an e.g. electromagnetic or electrostatic drive, the reflected beam and hence the laser focus performs Lissajous figures, in which in the oscillation reversal point of the one oscillation axis the other one does not have the velocity zero, but a finite value. Thus, with this movement the focus never comes to a standstill, which would lead to the undesired overlap of the excitation volumes of subsequent pulses.

Figure 10:
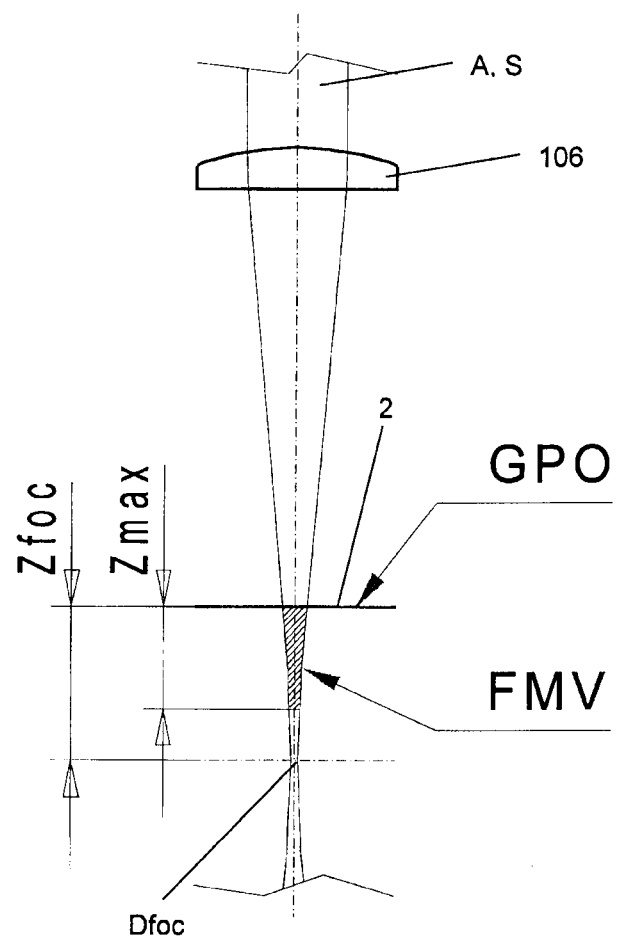
FIG. 10 shows a schematic diagram of a homogenized fluorescence excitation.

FIG. 10 shows a schematic representation (not to scale) of a homogenized fluorescence excitation, in which a laterally limited, but axially (vertically) expanded region ("FMV"=fluorescence measurement volume) of the object 2 is excited such that in axial direction the object 2 largely equally contributes to the optical signal S at least over a certain depth range. This optical signal S is recorded and integrated and can be evaluated and be processed further as an individual measured value, as spectrum or in multi-channel form with separate spectral bands ("band spectroscopy").

For recording purposes, the optical unit 103 (see e.g. FIG. 3) is moved exclusively in horizontal (lateral) direction (in X- or in X- and Y-direction) to the surface of the object 2 (a movement in vertical direction (Z) is not required, because the optical signal S is integrated over the depth).

To obtain a homogenized fluorescence excitation in a range designated as fluorescence measurement volume FMV, the parameters for the aperture of the objective 106, the focus diameter Dfoc and the focus depth Zfoc are adjusted to values within certain parameter ranges. Thus, a comparatively small aperture between 50 and 80 mrad (corresponding to the sine of half the opening angle of the aperture cone in air, i.e. without correction of the tissue refractive index) is chosen. The focus depth Zfoc advantageously is adjusted to a value between 100 µm and 450 µm, preferably 200 µm to 350 µm (measured in air, before placing the measurement system onto the skin, i.e. without correction of the tissue refractive index) and the focus diameter Dfoc is adjusted to a value between 6 µm and 10 µm, preferably between 7 µm and 9 µm.

The fluorescence measurement volume FMV extends from the tissue or sample surface GPO (object 2) axially into the depth down to an integration depth Zmax. The focus depth Zfoc is greater (deeper) than the integration depth Zmax.

Normally, the excitation radiation A in a tissue (object 2) is attenuated by scattering and absorption, so that tissue regions in a greater depth are excited to fluoresce less than regions close to the surface. In addition, the optical signal S from regions close to the surface is attenuated less on its way from the place of excitation to the measuring system than optical signals S from greater depths. Both of this leads to the fact that the measured optical signal S normally very predominantly is determined by regions close to the surface.

Surprisingly, it was found that with the chosen parameters for adjusting the focus depth Zfoc and the focus width Dfoc as well as the aperture a generally largely balanced contribution of all tissue layers within the fluorescence measurement volume FMV is obtained with an integration depth Zmax to the measured optical signal S. This is caused by the fact that the scaling rule of the two-photon excitation largely compensates the attenuation of the excitation radiation A and the optical signal S in the tissue with the intensity (at which the excitation probability increases in proportion to the square of the intensity).

Figure 11A:
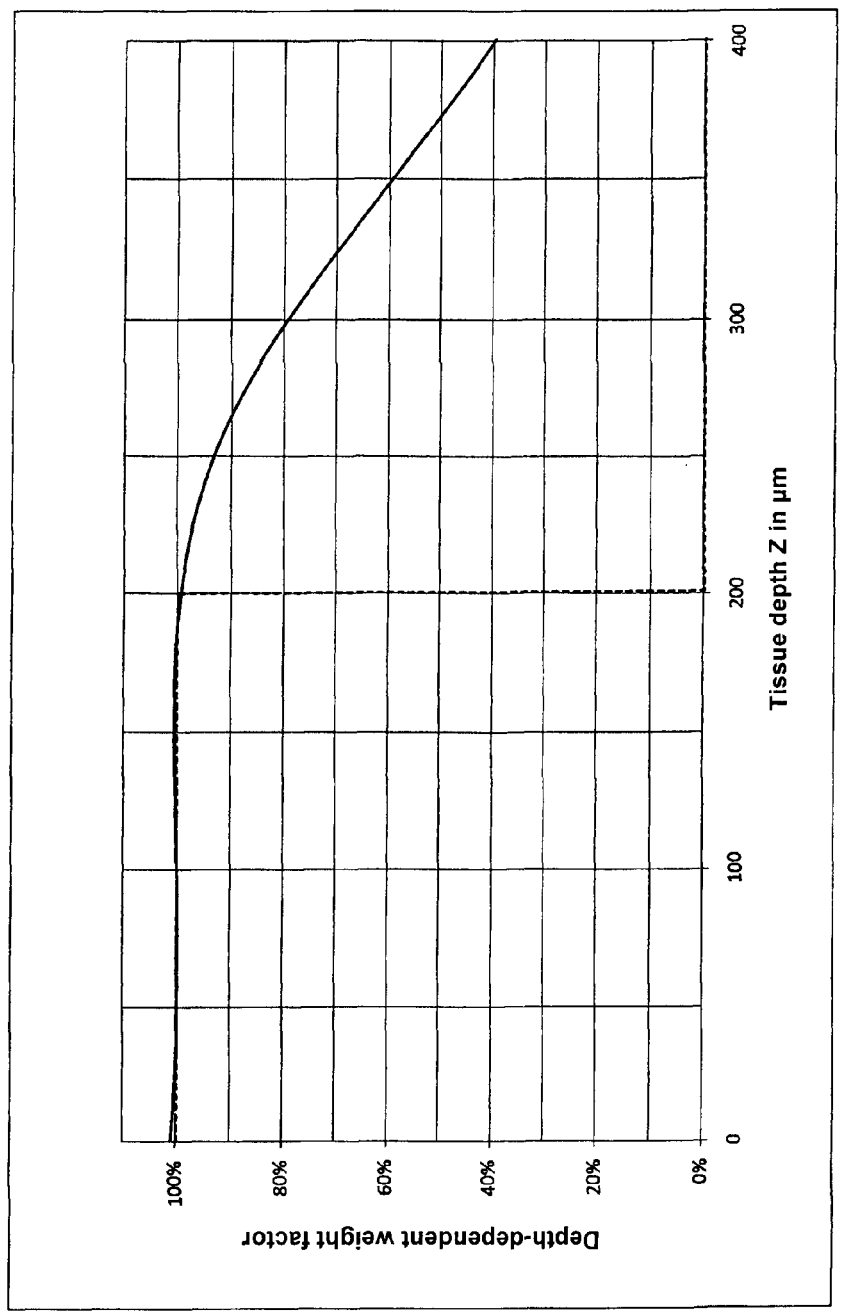
FIG. 11A shows a graphical representation of a depth-dependent weight factor in dependence on the tissue depth without depth cut-off.

FIG. 11A qualitatively shows the depth-dependent weight factor, which indicates to what extent certain depth regions contribute to the measured optical signal S. In this case, the focus depth Zfoc is adjusted to 300 µm, the integration depth amounts to Zmax=200 µm. For depths smaller than the integration depth (200 µm) chosen here, the contribution substantially is constant. Deeper regions, however, contribute to the optical signal S only to a reduced extent.

Figure 11B:
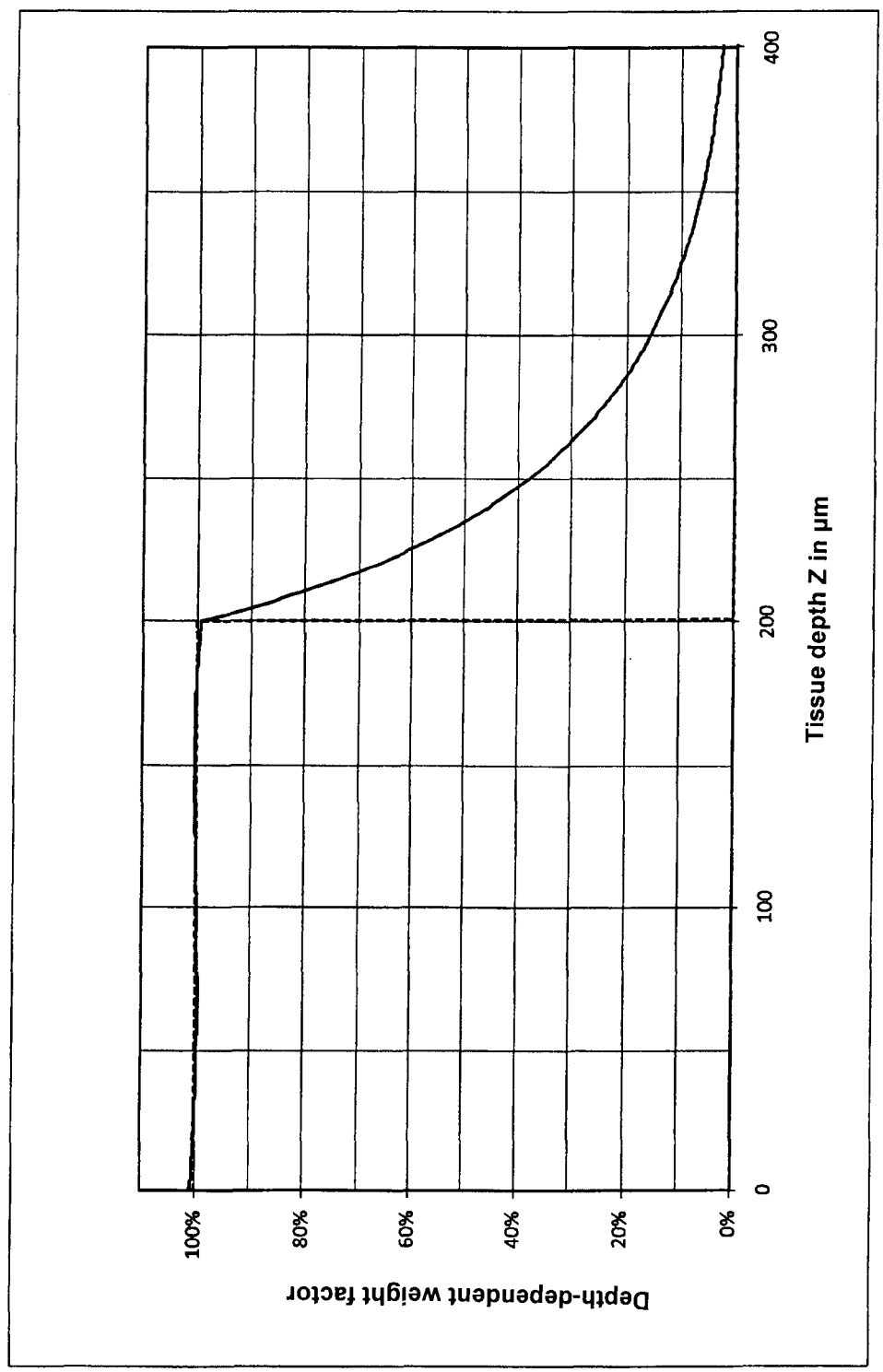
FIG. 11B shows a graphical representation of a depth-dependent weight factor in dependence on the tissue depth with depth cut-off.

The integration depth Zmax for the optical signal S in the object 2 (tissue) largely is limited by the fact that the two-photon effect no longer has a signal-amplifying effect after reaching the focus depth (the maximum integration depth (Zmax, down to which the signal contribution is approximately constant independent of the depth, is smaller than the focus depth Zfoc). By means of optical measures such as providing a diaphragm in the collection optic (collection efficiency limitation), this cut-off effect can even be intensified. A qualitative representation of the depth-dependent weight factor when using a diaphragm arranged in the beam path of the optical signal S for cutting off optical signals S from larger depths is shown in FIG. 11B.

The process of examining a lesion in a patient by using the device 1 basically is divided into two sections:
1. Recording a real image of the surface by means of the real image camera 111 (FIGS. 3 and 4) and deciding on the partial volumes to be examined in detail, including the definition of the recording line (scan track) in the image of the skin surface;
2. Performing the measurement for the actual microscopy sectional image along the scan track(s) defined in the real image.

The real image serves as an initial overview image, in order to enable a user to select a suitable recording line, and at the same time supplies additional documentary clinical information in the sense of the usual dermoscopy.

An examination of a patient by using the device 1 for example can proceed as follows:

An examination starts with the exact positioning of the patient module 10 (measuring head) attached to the supporting arm 11 at the patient. For search, the real image camera 111 is used, which supplies moving images of the skin surface. In a user interface, this video search image is displayed continually on the monitor 13 (FIG. 1.). After locking the patient module 10, a single overview image is taken and stored in a lesion data record.

To facilitate the definition of the plane for the sectional image to be recorded by a user, a selection region superimposed on the user interface can be inserted in the overview image, which corresponds to the actual region of the following microscopy image and can be defined and adapted by the user in the lateral length and position. In addition, the user must indicate the axial depth, in order to define a two-dimensional region for the sectional image to be recorded.

After defining the position of the sectional image, a calibration image initially can be made for automatically adjusting the laser power as a function of the axial depth; the actual microscopic image only is made thereafter. While recording the sectional image, the image obtained already is updated continually, in order to be able to stop false recordings in good time. After recording the sectional image, the user can record further images and add the same to the lesion data record.

The following data can be collected for example for examining a lesion of a patient:
Real image: 4 megapixel resolution in the high-quality photo mode; minimum of 1 megapixel resolution in the video mode, image frequency 25 fps; exposure time (in the photo mode) 50 ms or shorter.
Microscope image: The user defines a distance of 1-10 mm laterally with a maximum depth of 20 to 150 µm axially, wherein a measurement always starts at the skin surface (at a depth of 0 µm). For a lesion, the user can make any desired number of microscopy images.
To be able to detect possible displacements with respect to the first real image, a second real image is made after the actual microscopy sectional image and compared with the first one (so-called "pre-scan image" and "post-scan image").

A measurement for example can be made in a logical and chronological order as follows:
1. Initialization of the device 1:
   the device 1 is switched on,
   the linear motor which moves the optical unit 103 is brought into the starting position, the device 1 is prepared for recording (voltages are provided, components are checked and initialized, operability is established and signalized);
2. Start of the examination:
    patient data possibly are input by the operator,
    a measurement data record possibly is created by the operator;
3. Selection of the examination area and positioning of the patient module 10:
    the operator creates suitable conditions for a shot,
    a video image of the skin surface is displayed;
4. Recording of a real image ("pre-scan image"):
    as soon as the position is fixed (supporting arm 11 is locked and locking is indicated), the shot is triggered and the result is indicated to the user,
    the operator accepts or rejects the image (repetition in the latter case),
    the accepted image is stored as "pre-scan image", with the recorded data at the same time serving for a clinical evaluation of the lesion by the physician and for determination of the measurement area;
5. Definition of the recording line (scan track) in the real image of the skin surface:
    in the real image, the recording line (=sectional line of the X-Z scan field with the skin surface) is shown inserted as a line,
    the user can change the orientation and length of the recording line, in order to determine the lateral scan length (extension in X-direction) and scan position,
    the axial scan depth (extension in Z-direction) is adjusted via a control element (e.g. a slide control of a graphical user interface), wherein for example values between 0 and 150 µm are adjustable;
6. Calibration of the laser power:
    after fixing the scan data, the user can arrange for an automatic determination of the adaptation of the laser power in dependence on the scan depth or also manually define the same;
7. Performing the scan routine:
    by pressing a "Start" button, the microscopic scan is started, i.e.:
    first, the real image camera 111 is brought into a alternate position (manually or automatically),
    at the starting point of the recording line, the optical unit 103 starts the rasterization of the tissue,
    during the entire scan operation, safety functions (interruption, emergency shut-off, power monitoring) are continually monitored and the laser power is adapted continually according to the predefined function (calibration),
    simultaneously, a grey-scale picture of the measurement signal is built up in one or more windows (which are associated to the different spectral channels) on the monitor 13,
    in general, the scan routine ends automatically with a complete rasterization of the scan field and ready message on the monitor 13 (continued in item 8), or
    in a case of fault with termination and error message (continued in item 10);
8. Termination of the scan routine in the normal case:
    after the end of the scan operation, the system is switched into the real image mode, the real image camera 111 is brought into a recording position and a further real image is recorded; this "post-scan image" is compared with the associated stored "pre-scan image", wherein only with a sufficient accuracy of registration the actual scan image is "non-blurred" and usable;
    with a positive outcome of the examination, the user is offered to store the data or provide them with comments (continued with item 9) or to make a further shot at another or the same point (return to item 3);
9. End of the examination:
    if no further scans must be made or no further data must be processed, the device 1 is put into a rest condition (in which the motors are in the starting position, the shutter is closed and the PMTs are de-energized) and the application program is terminated.

The operation control can be realized by a software which can be implemented in an application program with a graphical user interface (GUI) and includes the following logical functions:
    initialization of the entire system, in particular self-test of the HW components and display of system status and errors; monitoring functions (laser power; laser condition);
    functions for the management of patient data, in particular a corresponding file and database structure which provides for the structured entry of patient-related data as well as associated administrative functions such as searching, changing, printing and cancelling data records;
    functions for the management of measurement data (real image; microscope image) and their allocation to patient data records;
    functions for the graphical representation of the measurement data from the different spectral channels and functions for the further processing of the measurement data (e.g. false color representation, range selection, ratio formation, edge recognition, etc.);
    functions for the control of the optical and the mechanical system;
    functions for the general process control, e.g. assistants for the user guidance during scans.

For control and signal processing, the control and processing unit 12 (see FIG. 1) preferably includes an electronic circuit which on the one hand has control over all sub-systems connected thereto and on the other hand controls the communication with the application software installed on a computer of the control and processing unit 12. By dividing the control of the connected components via the electronic circuit on the one hand and installing the application software on a separate computer (PC) on the other hand, it is possible to perform simple signal processing tasks and the control of the connected components such as photodiodes, shutters and stepper motors or their drivers on the part of the electronic circuit in real time, whereas more complex tasks are carried out by the application program on the computer without real time requirement and safety relevance. For a sufficient flexibility, the control and processing unit 12 should be designed programmable.

For protection of the detectors 1221, 1222, 1223 (for example configured as PMTs) of the detector module 121, it can be provided to measure the brightness outside the patient module 10 by means of a photodiode. If the same lies above an admissible value, i.e. if potentially too much light is transported via the optical fiber 10, a control voltage for the detectors 1221, 1222, 1223 is reduced and an error message is sent to the application program To exclude an exposure of the human eye to laser light, it can be provided to open the shutter provided for controlling the exposure only when a mechanical (switch) or optical (light barrier) device signals a close contact of the patient module 10 with the object 2 to be examined. Whether or not a contact exists can be communicated to the application program.

The device 1 as an imaging medical system represents the data obtained in the form of an image, wherein the data are made available or represented as promptly as possible (ideally in real time). System conditions such as error messages are visualized in corresponding displays.

On the input side, an application software can be formed to process user inputs intuitively and related to the respective object. This means in particular that the positioning of a measurement field (Region of Interest, ROI) can be effected directly in the previously recorded real image and that an area selection in an image (real image or microscope image) is supported with suitable zoom and scroll functions as well as drag-and-drop. In addition, tools can be provided which make the necessary calculations for a user and support the evaluation of the images (measurement of sizes and distances). An examination can be interrupted or terminated by a user at any time via the application software. Depending on the operating mode (scan or evaluation), the software provides corresponding operating masks.

On the output side, the application software is formed to indicate every system change and directly realize a screen update. This includes e.g. the operating condition in general, the state of movement of the motors, the progress of a measurement program and the prompt set-up of real and microscope images. Due to the geometry of the recorded sectional images (in which the image width is a multiple of the image height, e.g. with a ratio of about 1:50), it is required that a microscope image is represented either in partial strips located one beside the other or as a section (as long as possible).

The invention is not limited to the exemplary embodiments described above. In particular, the described methods and devices are not limited in principle to the two-photon excitation, but can also be used for the three- or multi-photon microscopy or spectroscopy.

The invention claimed is:

1. A device for multi-photon fluorescence microscopy for obtaining information from biological tissue, comprising:
   a laser unit for generating an excitation radiation,
   an optical unit which is formed to focus the excitation radiation for generating an optical signal at different locations in or on an object to be examined,
   a control and processing unit,
   a patient module connected to the control and the processing unit, which for examining the object can be placed relative to the object, wherein the optical is part of the patient module, and
   a detector module for detecting the optical signal from the region of the object,
   wherein the optical unit for generating the optical signal at different locations in or on the object is movable within a housing of the patient module in at least one direction relative to the object,
   wherein the laser unit is part of the control and processing unit and an optical fiber connects the laser unit with the patient module for transmitting the excitation radiation towards the optical unit,
   wherein the laser unit generates an excitation radiation with a first wavelength to transmit the excitation radiation through the optical fiber, and a frequency doubler is arranged in the patient module for halving the wavelength of the excitation radiation prior to the optical unit,
   wherein from the received optical signal is a sectional image of the object is generated pixel by pixel at different locations of the object,
   wherein for generating the sectional image pixel by pixel the object is exposed to the excitation radiation in a triggered manner, and
   wherein the pixel size of the sectional image pixel by pixel is determined in horizontal direction by the focus of the excitation radiation and by adjusting the triggering, and in vertical direction by the waist length of the focused excitation radiation,
   wherein the pixel size is adjustable by a beam expansion of the excitation radiation and by adjusting the triggering.

2. The device according to claim 1, wherein during a movement of the optical unit for generating the optical signal the angular position of the optical axis of the excitation radiation falling onto the object is not changed.

3. The device according to claim 1 or 2, wherein the optical unit is movable in horizontal direction and/or in vertical direction relative to a surface of the object facing the optical unit.

4. The device according to claim 3, wherein the optical unit includes an objective for focusing the excitation radiation at a location in or on the object, wherein the objective is movable in vertical direction relative to the surface of the object.

5. The device according to claim 1, wherein for generating a vertical sectional image pixel by pixel the optical unit is at least partly continuously movable in horizontal direction and/or in vertical direction relative to the object.

6. The device according to claim 1, wherein the patient module is connected with the control and processing unit via a supporting arm, which for examining the object can be placed relative to the object.

7. The device according to claim 6, wherein the optical unit is movable independent of the optical fiber for transmitting the excitation radiation.

8. The device according to claim 1, wherein the optical unit is formed for collecting the optical signal.

9. The device according to claim 8, wherein via an optical fiber the optical unit is connected with the detector module for transmitting the recorded optical signal to the detector module.

10. The device according to claim 9, wherein the optical fiber for transmitting the recorded optical signal to the detector module differs from an optical fiber provided for transmitting the excitation radiation.

11. The device according to claim 8, characterized wherein the detector module is formed to evaluate the different signal components for imaging and/or for the spectroscopic analysis.

12. The device according to any of the preceding claim 1, wherein the detector module is formed to split up the received optical signal into a plurality of different signal components in different wavelength ranges and for this purpose includes one or more dichroic filter elements.

13. A method for multi-photon fluorescence microscopy for obtaining information from biological tissue, in which
   a laser unit generates an excitation radiation,
   an optical unit focuses the excitation radiation for generating an optical signal at different locations in or on an object to be examined,
   a control and processing unit,
   a patient module connected to the control and the processing unit, which for examining the object can be placed relative to the object, wherein the optical is part of the patient module, and a detector module detects the optical signal from the region of the object, wherein the optical unit for generating the optical signal in or on the object is moved within a housing of the patient module in at least one direction relative to the object, wherein the laser unit is part of the control and processing unit and an optical fiber connects the laser unit with the patient module for transmitting the excitation radiation towards the optical unit, and wherein the laser unit generates an excitation radiation with a first wavelength to transmit the excitation radiation through the optical fiber, and a frequency doubler is arranged in the patient module for halving the wavelength of the excitation radiation prior to the optical unit, wherein from the received optical signal is a sectional image of the object is generated pixel by pixel at different locations of the object, wherein for generating the sectional image pixel by pixel the object is exposed to the excitation radiation in a triggered manner, and wherein the pixel size of the sectional image pixel by pixel is determined in horizontal direction by the focus of the excitation radiation and by adjusting the triggering, and in vertical direction by the waist length of the focused excitation radiation, wherein the pixel size is adjustable by a beam expansion of the excitation radiation and by adjusting the triggering.

14. The method according to claim 13 at wherein the optical unit is moved exclusively in horizontal direction to the surface of the object and the optical signal is integrated in vertical direction.

* * * * *